United States Patent
Shimamura et al.

(10) Patent No.: US 8,422,071 B2
(45) Date of Patent: Apr. 16, 2013

(54) INFORMATION CONVERSION METHOD, INFORMATION CONVERSION APPARATUS, AND INFORMATION CONVERSION PROGRAM

(75) Inventors: Kenta Shimamura, Itami (JP); Po-Chieh Hung, Hachioji (JP); Yorihiro Yamaya, Hino (JP); Shin-ichiroh Kitoh, Hokuto (JP); Mayumi Takeda, Kyoto (JP)

(73) Assignee: Konica Minolta Holdings, Inc., Tokyo (JP)

( * ) Notice: Subject to any disclaimer, the term of this patent is extended or adjusted under 35 U.S.C. 154(b) by 607 days.

(21) Appl. No.: 12/452,982

(22) PCT Filed: Aug. 5, 2008

(86) PCT No.: PCT/JP2008/064015
§ 371 (c)(1),
(2), (4) Date: Feb. 1, 2010

(87) PCT Pub. No.: WO2009/020115
PCT Pub. Date: Feb. 12, 2009

(65) Prior Publication Data
US 2010/0134810 A1      Jun. 3, 2010

(30) Foreign Application Priority Data

Aug. 7, 2007 (JP) ................. 2007-205955
Jan. 17, 2008 (JP) ................. 2008-008401

(51) Int. Cl.
*H04N 1/60* (2006.01)
*H04N 1/46* (2006.01)

(52) U.S. Cl.
USPC ........................ 358/1.9; 358/517

(58) Field of Classification Search ............ 358/1.9, 358/1.14, 1.18, 1.16, 517, 529; 382/100, 382/254, 167; 400/61, 62; 709/203, 228
See application file for complete search history.

(56) References Cited

U.S. PATENT DOCUMENTS 7,605,930 B2 * 10/2009 Suzuki et al. ................. 358/1.14
2003/0095705 A1    5/2003 Weast
2004/0085327 A1    5/2004 Jones et al.

FOREIGN PATENT DOCUMENTS

| JP | 2001-257867 A | 9/2001 |
| JP | 2001-293926 A | 10/2001 |
| JP | 2003-223635 A | 8/2003 |
| JP | 2004-178513 A | 6/2004 |
| JP | 2004-266821 A | 9/2004 |

(Continued)

OTHER PUBLICATIONS

Extended European search report (EESR) dated Apr. 15, 2011 in English for Application No. 08792201.9.

(Continued)

*Primary Examiner* — Charlotte M Baker
(74) *Attorney, Agent, or Firm* — Holtz, Holtz, Goodman & Chick, P.C.

(57) ABSTRACT

Reproduction can be adjusted according to the degree of achromatopsia and the color distribution of an image, and color reproduction approximate to the vision of normal persons is provided to achromates. Different textures are added to respective regions (similar and hardly indistinguishable regions) which have different colors but conduce to similar result of light-reception by a light receiving device according to the differences of the original colors. The textures include a pattern of angle, hatching, or contrast each different according to the difference of the original color.

31 Claims, 20 Drawing Sheets

FOREIGN PATENT DOCUMENTS

| | | |
|---|---|---|
| JP | 2005-051405 A | 2/2005 |
| JP | 2005-182432 A | 7/2005 |
| JP | 2005-190009 A | 7/2005 |
| JP | 2005-346273 A | 12/2005 |
| JP | 2006-154982 A | 6/2006 |
| WO | WO 2005/055893 A1 | 6/2005 |

OTHER PUBLICATIONS

K. Wakita et al, "SmartColor: Disambiguation Framework for the Colorblind", *In Assets '05: Proc. of the International ACM SIG ACCESS Conference on Computers . . .* , NY, USA, pp. 158-165 (2005).

* cited by examiner

RED BEFORE CONVERSION

GREEN BEFORE CONVERSION

RED AFTER CONVERSION
(THIN RED + DARK RED INCLINED LINES)

GREEN AFTER CONVERSION
(THIN GREEN + DARK GREEN INCLINED LINES)

FIG. 7
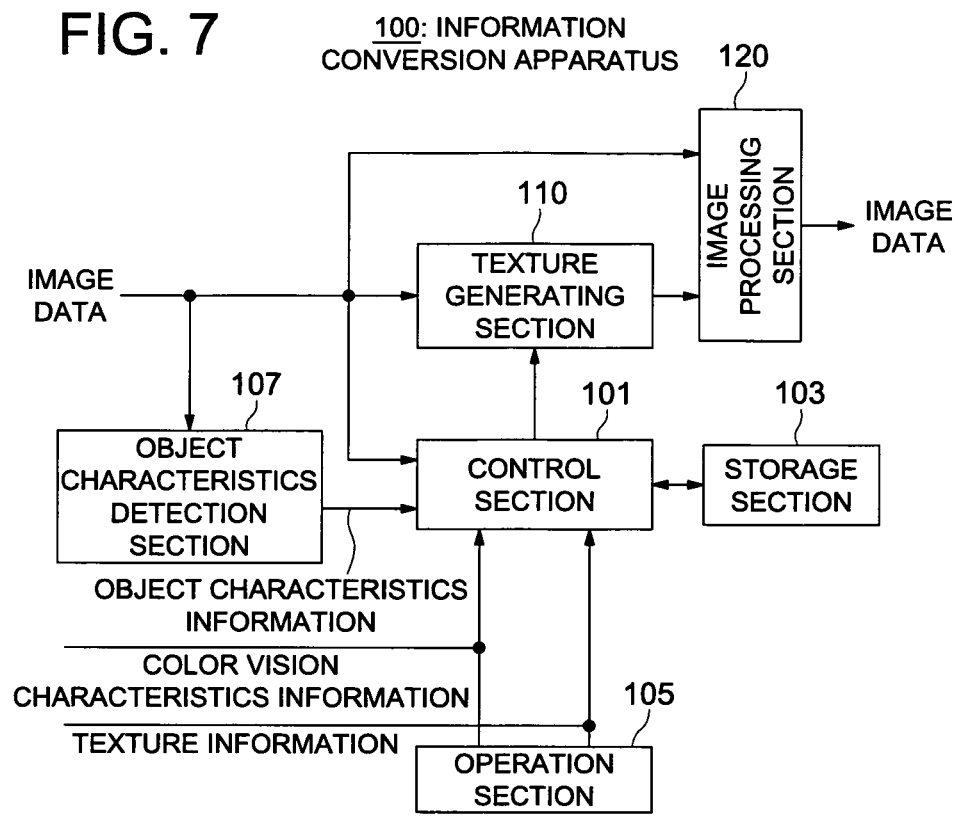
FIG. 8a  FIG. 8b  FIG. 8c
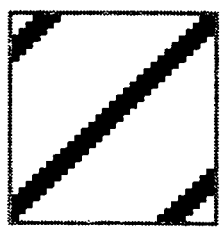 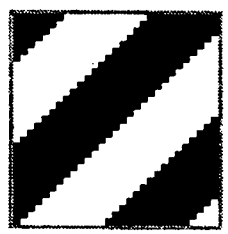 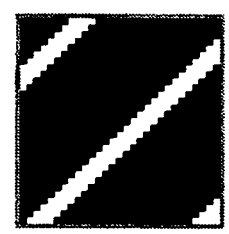
FIG. 9a  FIG. 9b  FIG. 9c
 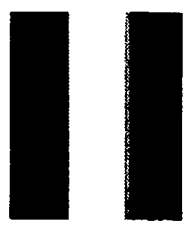 

FIG. 10

| BROAD CLASSIFICATION ACCORDING TO NUMBER OF COLORS OF ABNORMALITY | CLASSIFICATION ACCORDING TO NATURE OF COLOR VISION | | |
|---|---|---|---|
| NORMAL TRICHROMAT | NORMAL TRICHROMAT(N) | | |
| UNOMALOUS TRICHROMAT | PROTANOMALOUS TRICHROMAT(PA) | DEUTERANOMALOUS TRICHROMAT(DA) | TRITANOMALOUS TRICHROMAT(TA) |
| DISCHROMAT | PROTANOPE(P) | DEUTERANOPE(D) | TRITANOPE(T) |
| MONOCHROMAT | CONE MONOCHROMAT | ROD MONOCHROMAT | |

COLOR CONFUSION LINE OF DICHROMATIC
TYPE COLOR VISION ABNORMALITY PERSONS
FROM ABOVE, P, D, T, AND W INDICATE WHITE
COLOR AND N INDICATES NEUTRAL POINT.

THE HATCHING ANGLE IS NOT THE EXPECTED ANGLE

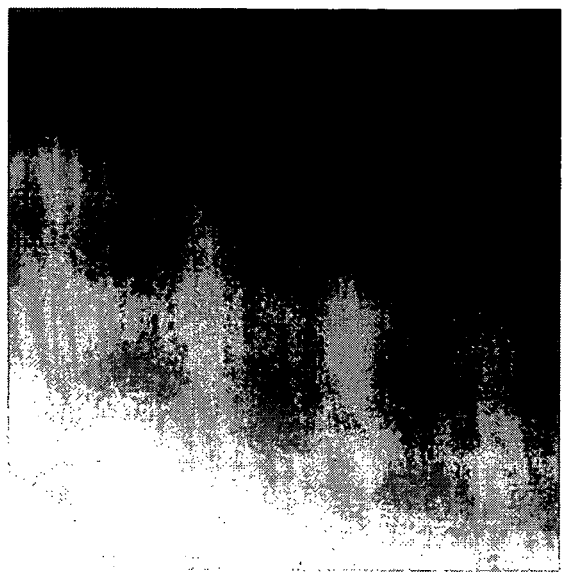
FIG. 24a
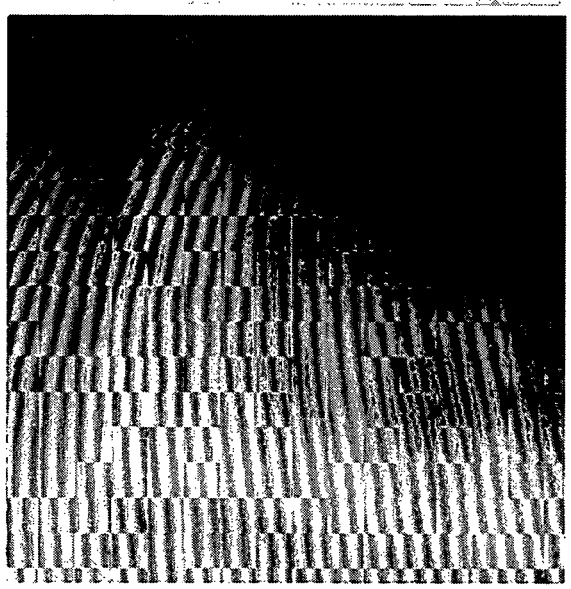
FIG. 24b
FIG. 25a
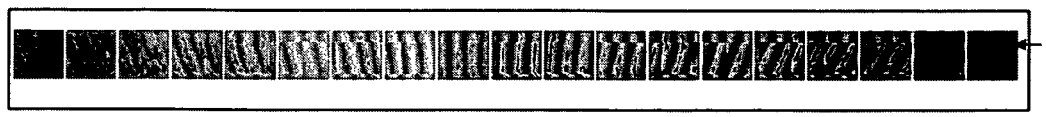
FIG. 25b

INFORMATION CONVERSION METHOD, INFORMATION CONVERSION APPARATUS, AND INFORMATION CONVERSION PROGRAM

This application is the United States national phase application of International Application PCT/JP2008/064015 filed Aug. 5, 2008.

TECHNICAL FIELD

The present invention relates to information conversion methods, information conversion apparatuses, and information conversion programs that make chromatic image display possible in a state that is suitable for observation by color vision deficient persons.

Further, the present invention relates to information conversion methods; information conversion apparatuses, and information conversion programs that, when a chromatic image display is made as an achromatic image display, make it possible to guess the original chromatic image display.

PRIOR ART

Color vision deficiency is one of the disorders of the eye, and is one in which there is some abnormality in the recognition of and discrimination between colors due to defects or abnormality of cone photoreceptor cells that recognize color.

Here, color vision deficient persons, as is described in Table 9.1 "Classifications of color vision deficient persons and abbreviated symbols for them" (p. 189) of "Fundamentals of Color Engineering" (p. 189) authored by Mitsuo Ikeda, Asakura Shoten, are classified according to the photoreceptor cells of red (L cone cells), green (M cone cells), and blue (S cone cells), and according to their sensitivities (see FIG. 10).

Here, any person having no sensitivity in any of the photoreceptor cells is called color blind, which is classified as type P in the case of L cone cells, type D in the case of M cone cells, and type T in the case of S cone cells.

When any of the sensitivities is low, the situation is called color weakness which is respectively classified into types PA, DA, and TA. The color vision characteristics of types P, D, and T are such that, as is described in Table 9.13 "Color confusion line of dichromatic color vision deficient persons" (p. 205) of "Fundamentals of Color Engineering" authored by Mitsuo Ikeda, Asakura Shoten, the colors present on this line (color confusion line) appear as a completely identical color, and it is not possible to distinguish between them (see FIG. 11).

Such color vision deficient persons cannot distinguish between the colors of an image viewed by a normal color vision person in the same manner, and hence image display or image conversion is necessary for color vision deficient persons.

Proposals for this type of color vision abnormality have been made in the following Non-patent Document and Patent Documents.

Further, a phenomenon similar to that of color vision abnormality can occur even for normal persons under light sources with restricted spectral distributions. Further, this phenomenon can also occur when photographing using a camera.

Non-patent Document 1: SmartColor (K. Wakita and K. Shimamura, SmartColor: Disambiguation Framework for the Colorblind. In Assets '05: Proc. Of the 7th International ACM SIG ACCESS Conference on Computers and Accessibility, pages 158-165, NY, USA, 2005.

Patent Document 1: Unexamined Japanese Patent Application Publication No. 2004-178513.
Patent Document 2: Unexamined Japanese Patent Application Publication No. 2007-512915.
Patent Document 3: Unexamined Japanese Patent Application Publication No. 2003-223635.
Patent Document 4: Unexamined Japanese Patent Application Publication No. 2004-266821.
Patent Document 5: Unexamined Japanese Patent Application Publication No. 2005-182432.

DISCLOSURE OF THE INVENTION

Problems to be Solved by the Invention

The technology described in the above Non-patent Document 1 improves the ease of distinguishing by changes in the color by converting the display into colors that can be distinguished by color vision abnormal persons. In this case, since there is a trade-off between the amount of color change for color vision abnormal persons and the colors recognized by normal color vision persons, when conversion is made into colors that can be recognized by color vision abnormal persons, the color changes largely, and there will be a big change in the impression from the original display. Because of this, it is difficult to share documents between normal persons and color vision abnormal persons. Although there is a setting of making the color change as low as possible, in that case, there is not much improvement in the ease of distinguishing for color vision abnormal persons. In addition, since the color which is changed is determined according to the content of the color of the display, there is a big problem that the original color changes.

The technology described in the above Patent Document 1 not only classifies the display data into those for which color—shape conversion is made and those for which this conversion is not made, but also, further classifications are made in terms of the shape such as point, lines, surfaces, etc., a table is possessed that has the shapes corresponding to the predetermined colors, and the result of this classification is converted into shapes by referring to the table.

In the above Patent Document 1, the method of determining the shape is arbitrary, and the system is such that the interpretation is made by seeing the legend.

Since the colors in the color space are made to be distinguished by shapes for each surface, line, or point, there is the problem that the candidates for shapes become insufficient. Further, since the ease of distinguishing the shapes has not correlation with the distinguishing of the original colors, there will be a big difference in the ease of distinguishing among objects relative to normal color vision persons, the feelings cannot be shared with normal persons.

In addition, when an object that is of a single color is converted in a shape, very often there is an increase into multiple colors, while it becomes possible to distinguish from an object of the roughly the same color because of multiple colors, in that case even if one color is maintained with the original color, the overall color of the object becomes a synthesis of multiple colors, and can sometimes become different from the original color.

In addition to this, since there is no clear rule for the parameters of the color and determining the shape, the person seeing the display cannot understand the correspondence between colors and shapes unless there is a legend, and it is not possible to interpret the type of color. Even when there is a legend, it is difficult to establish the correspondence. Since there is no common part in the methods of determining the shapes respectively for points, lines and surfaces, it becomes more difficult.

Further, there is also a big problem that it is not possible to express accurately fine differences in the colors such as that there is no continuity, or that it is not possible to distinguish between fine colors, etc.

The technology described in Patent Document 2 is an apparatus that photographs the subject and converts in the display so that it can be distinguished by a color vision abnormal person. This is a method in which the areas with roughly the same color as the (one or more) colors of the locations identified by the user within the photographed subject are made to be distinguished from other areas. This has distinguishing using texture or blinking.

In the above Patent Document 2, the method of determining the shape is arbitrary, and the details of the concrete example given have not been described.

Firstly, since the ease of distinguishing the shapes is not correlated with the ease of distinguishing the original colors, the ease of distinguishing between objects is largely different from those of normal color vision persons, and it is not possible to share the feelings with normal persons.

In addition, the original color cannot be maintained. When an object of a single color is converted into a shape, very often there is an increase into multiple colors, while it becomes possible to distinguish from an object of the roughly the same color because of multiple colors, in that case even if one color is maintained with the original color, the overall color of the object becomes a synthesis of multiple colors, and can sometimes become different from the original color.

In addition to this, since there is no clear rule for the parameters of the color and determining the shape, the person seeing the display cannot understand the correspondence between colors and shapes unless there is a legend, and it is not possible to interpret the type of color. Even when there is a legend, it is difficult to establish the correspondence.

Further, there is also a big problem that it is not possible to express accurately fine differences in the colors such as that there is no continuity, or that it is not possible to distinguish between fine colors, etc.

The above Patent Document 3, in a machine using the RGB video signals, uses the method of increasing each of the RGB ratios in the case of a person with color vision weakness.

Here, in the above Patent Document 3, a method has been described of making the gain of the RGB signals strong of the video process amplifier according to the extent of the color weakness. While in this method it has been made easy for a person with color vision abnormality to distinguish the colors by emphasizing the colors, the effect of all the colors in the image will be present. Because of this, there is a problem that the original color cannot be maintained.

Further, this method is limited to color vision weakness (trichromacy type of color vision abnormal persons). In addition, there is the problem that this method cannot be used unless investigation is made as to which is the type among the many types of color vision characteristics in color weakness.

In the above Patent Document 4, in FIG. 11, distinguishing is made possible by converting the color so that it is not on the color confusion line.

In the above Patent Document 4, the colors in the image are classified into several colors which are plotted on the color confusion line of FIG. 11, and when they are on the color confusion line, the center of the color confusion line is changed by changing the angle of the center so that it is not on the color confusion line. However, this method, similar to the Non-patent Document 1, has the problem that distinguishing is difficult while maintaining the original color since there is a trade off between distinguishing and maintaining the original color.

Further, since clustering (classification) is done for the main color (the mainly generated color), fine differences in the color will become impossible to distinguish. There is a problem that continuity and gradation will be disturbed.

In the above Patent Document 5, for color blind persons, the colors are converted so that the degrees of color mixture and color differences become small. This above Patent Document 5 is a method of converting colors for color vision deficient persons, and this method is one in which the sum of the difference with the original color and the extent to which the converted color lies on the color confusion line is made as small as possible. However, similar to the above Non-patent Document 1, this method has the problem that distinguishing is difficult while maintaining the original color since there is a trade off between distinguishing and maintaining the original color.

Further, the method of converting colors has only been described as minimizing the mathematical equation, no concrete method of conversion has been described. In addition, even this method has the problem that continuity and gradation will be disturbed.

Further, problems similar to the above cases occur even when making the chromatic image display as an achromatic image display, that is, when a color image data is printed out in monochrome. In other words, when the color image data in the computer is not printed in a color printer but is printed in a monochrome printer, even when the original colors are different, they are merely reproduced as monochrome light and dark variations. In addition, the same problem occurs when a color original document is copied in a monochrome copying machine.

The present invention has been made in order to solve the above problems, and the purpose of the present invention is to provide an information conversion method, an information conversion apparatus, and an information conversion program that realizes a chromatic image display, in a condition suitable for observation by normal persons and persons with color vision abnormality, that can be distinguished close to the normal viewing equivalent that observed by normal persons.

Further, the purpose of the present invention is to provide an information conversion method, an information conversion apparatus, and an information conversion program that, even when color image data is output in monochrome, makes it possible to distinguish the original chromatic condition.

Means For Solving The Problems

The present invention for solving the above problems is one as described below.

According to a first aspect of the present invention an information conversion method includes: adding textures of different states to areas of similar colors according to differences in the original colors, regarding the areas which are different in original colors and similar in light reception results on a light reception side.

According to the information conversion method of the present invention, the textures have patterns or hatching with different angles according to the differences in the original colors.

In addition, according to the information conversion method of the present invention, the textures have different contrasts according to the differences in the original colors.

Still further, according to the information conversion method of the present invention, the textures change with time according to the differences in the original colors.

Yet still further, according to the information conversion method of the present invention, the textures move in different directions according to the differences in the original colors.

Yet still further, according to the information conversion method of the present invention, the textures are combinations of at least any two among textures having patterns or hatching with different angles according to the differences in the original colors, textures having different contrasts according to the differences in the original colors, textures that change with time according to the differences in the original colors, textures that move in different directions according to the differences in the original colors.

Yet still further, according to the information conversion method of the present invention, the textures are textures of states that change approximately continuously according to the differences in the original colors.

Yet still further, according to the information conversion method of the present invention, an average color in the areas in which textures have been added approximates the original color.

Yet still further, according to the information conversion method of the present invention, the areas in the image with similar colors results of light reception have the colors lying on the same color confusion line.

According to a second aspect of the present invention, an information conversion apparatus includes a texture generating section generating textures of different states to areas of similar colors according to differences in the original colors, regarding the areas which are different in original colors and similar in light reception results on a light reception side, and an image processing section synthesizing and outputting the textures generated by the texture generating section and the original image.

In addition, according to the information conversion apparatus of the present invention, the texture generating section generates textures having patterns or hatching with different angles according to the differences in the original colors.

Still further, according to the information conversion apparatus of the present invention, the texture generating section generates textures having different contrasts according to the differences in the original colors.

Yet still further, according to the information conversion apparatus of the present invention, the texture generating section generates textures that change with time according to the differences in the original colors.

Yet still further, according to the information conversion apparatus of the present invention, the texture generating section generates textures that move in different directions according to the differences in the original colors.

Yet still further, according to the information conversion apparatus of the present invention, the texture generating section generates textures which are combinations of at least any two among textures having patterns or hatching with different angles according to the differences in the original colors, textures having different contrasts according to the differences in the original colors, textures that change with time according to the differences in the original colors, textures that move in different directions according to the differences in the original colors.

Yet still further, according to the information conversion apparatus of the present invention, the texture generating section generates textures of states that change approximately continuously according to the differences in the original colors.

Yet still further, according to the information conversion apparatus of the present invention, the texture generating section generates textures of average color in the areas in which textures have been added approximates the original color.

Yet still further, according to the information conversion apparatus of the present invention, the texture generating section generates textures of different states according to the differences in the original colors as the areas in the image with similar colors results of light reception have the colors lying on the same color confusion line.

According to a third aspect of the present invention, a computer readable recording medium stores a program which causes a computer to realize a function as a texture generating section generating textures of different states to areas of similar colors according to differences in the original colors, regarding the areas which are different in original colors and similar in light reception results on a light reception side, and an image processing section synthesizing and outputting the textures generated by the texture generating section and the original image.

According to a fourth aspect of the present invention an information conversion method comprises the step of adding textures of different angles according to differences in the original colors for each area that is constituted from a previously set plurality of pixels, regarding the areas which are different in original colors and similar in light reception results on a light reception side.

According to the information conversion method of the fourth aspect of the present invention, the textures have patterns or hatching with different angles according to the differences in the original colors.

In addition, according to the information conversion method of the fourth aspect of the present invention the areas are generated by segmenting the image in the form of a grid.

Still further, according to the information conversion method of the fourth aspect of the present invention, the method further comprises the step of dividing the areas into a plurality of segments according to the difference in the color, adding angles for each of those segments.

Yet still further, according to the information conversion method of the fourth aspect of the present invention, the method further comprises the step of judging the presence or absence of noise or dither inside the area, and not dividing the parts in which noise or dither is judged to be present into segments.

Yet still further, according to the information conversion method of the fourth aspect of the present invention, the dividing of the segments is not made when the color difference between neighboring pixels within the same area is judged to be less than a prescribed value.

According to a fifth aspect of the present invention an information conversion apparatus comprises a texture generating section generating textures of different angles according to differences in the original colors for each area that is constituted from a previously set plurality of pixels, regarding the areas which are different in original colors and similar in light reception results on a light reception side, and an image processing section synthesizing and outputting the textures generated by the texture generating section and the original image.

According to the information conversion apparatus according to the fifth aspect of the present invention, the texture generating section generates textures having patterns or hatching with different angles according to the differences in the original colors.

In addition, according to the information conversion apparatus according to the fifth aspect of the present invention, the texture generating section generates textures with different angles for each area generated by segmenting the image in the form of a grid.

Still further, according to the information conversion apparatus according to the fifth aspect of the present invention, the texture generating section divides the areas into a plurality of segments according to the difference in the color, and generates textures having patterns or hatching with different angles for each of the segments.

Yet still further, according to the information conversion apparatus according to the fifth aspect of the present invention, the texture generating section judges the presence or absence of noise or dither inside the area, and does not divide the parts in which noise or dither is judged to be present into segments.

Yet still further, according to the information conversion apparatus according to the fifth aspect of the present invention, the texture generating section does not divide the segments when the color difference between neighboring pixels within the same area is judged to be less than a prescribed value.

According to a sixth aspect of the present invention a computer readable recording medium stores a program which causes a computer to realize a function as texture generating section generating textures of different angles according to differences in the original colors for each area that is constituted from a previously set plurality of pixels, regarding the areas which are different in original colors and similar in light reception results on a light reception side, and an image processing section synthesizing and outputting the textures generated by the texture generating section and the original image.

According to the information conversion method of the present invention color image data is printed out by monochrome printing.

According to the information conversion apparatus of the present invention, color image data is printed out by monochrome printing.

According to the computer readable recording medium of the present invention color image data is printed out by monochrome printing.

Further, in each of the above inventions, regarding the area in the image with different colors but the results of light reception on the light receiving side are similar, that is, regarding the color vision characteristics, or, regarding the types of textures, it is desirable that textures are generated based on the instructions from a control section.

Effect of the Invention

The following effects can be obtained by an information conversion method, an information conversion apparatus, and an information conversion program according to the present invention.

In the present invention, regarding the areas in the image that are difficult to distinguish from each other because, while being of different colors the results of light reception in the light receiving side are similar, by adding textures of different states to those areas that are similar, it is possible to realize a chromatic image display, in a condition suitable for observation by persons with color vision abnormality, that can be distinguished close to the normal viewing equivalent that observed by normal persons.

Here, the areas in the image in which the results of light reception are similar are colors that lie on the same color confusion line.

Further, the ability to distinguish is enhanced further by making said textures have patterns or hatching with different angles according to the differences in the original colors. In addition, by defining the angles in advance, it becomes possible to memorize, and it is possible to distinguish the differences in color continuously without having to refer to a legend.

Further, the ability to distinguish is enhanced further by making said textures have different contrasts according to the differences in the original colors.

Further, the ability to distinguish is enhanced further by making said textures change with time according to the differences in the original colors.

Further, the ability to distinguish is enhanced further by making said textures move in different directions according to the differences in the original colors.

Further, the ability to distinguish is enhanced further by making said textures have a combination of two or more of—patterns or hatching with different angles according to the differences in the original colors, different contrasts according to the differences in the original colors, change with time or move at different speeds according to the differences in the original color, or move in different directions or with different speeds according to the differences in the original colors.

Further, it becomes possible to distinguish finely close to the original colors by making said textures have roughly continuously changing conditions according to the differences in the original color.

Further, because of the addition of the above textures, not changing the average color in the region in which this addition was made from the original color or making it approximate the original color is desirable because it does not affect viewing by a normal person and the original view is retained.

Further, the above color confusion line method of the present invention is a method that has a particularly large effect on color blindness. Since color confusion lines are had by color blind persons, the color confusions of PA, DA, and TA who are color vision weak persons are respectively similar to the color confusions of P, D, and T who are color blind persons, and with the method of the present invention, it is possible to solve the display for both color blind persons and color vision weak persons.

Further, regarding the areas in the image that are difficult to distinguish because, while being the same colors, the results of light reception in the light receiving side are similar, for each area constituted from a predetermined plurality of pixels, by adding textures with different angles according to the differences in the original colors, since the angle of the texture is determined for a specific area of that region, the ability for visual recognition of that angle increases.

In other words, when gradations or noise is present in the image, although a phenomenon similar to moire patterns becomes likely to occur because the angle of the texture changes according to the color noise of the original image, since the angle of the texture is given for each area of a prescribed number of pixels, such problems will be avoided.

Further, as described above, since the angle of the texture is determined for each area of a predetermined prescribed number of pixels, a large memory is not necessary for superimposing a texture such as hatching, etc., on the image. For example, it becomes possible to process the image only with a quantity of memory by dividing the image into strips so that the prescribed pixel width is incorporated.

Further, by dividing within the area into segments according to the color difference, and by giving said different angles for each of those segments, hatching is done neatly for each color in a graph, etc., and for gradations, the hatching is done in the form of an average within the grid (inside a rectangular block).

Further, in the case in which the pattern has become a checkered pattern due to dither, etc, or in the case of a simple vertical or horizontal stripe pattern, since the appearance is that of an average color, upon judging the presence of dither or noise, it is not treated as a segment, and textures such as hatching, etc, are added in a condition that is close to visual appearance.

Further, at the time of making a monochrome output of color image data, by carrying out addition of the above textures such as hatching, etc., it is possible to recognize the original chromatic condition in the case of a monochromatic image or in the case of a fully color blind person.

BRIEF DESCRIPTIONS OF THE DRAWINGS

Figure 3A:
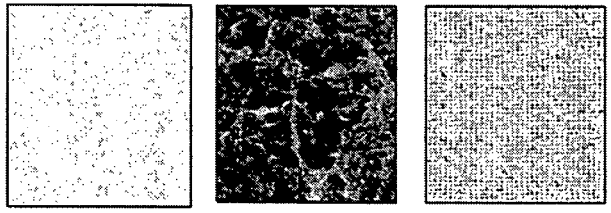
Figure 3B:
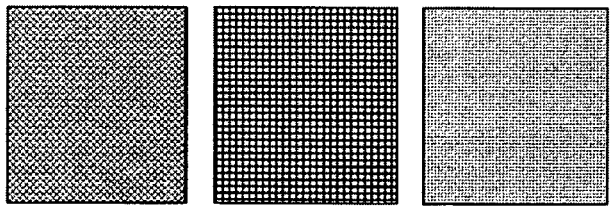
Figure 3C:
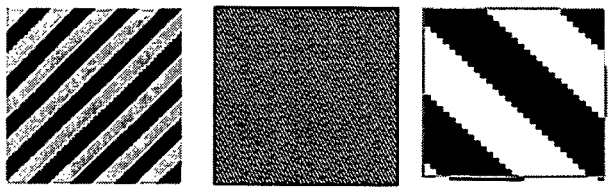

FIG. 3a is an explanatory diagram showing some examples of textures of a first preferred embodiment of the present invention. FIG. 3b is an explanatory diagram showing some examples of textures of a first preferred embodiment of the present invention. FIG. 3c is an explanatory diagram showing some examples of textures of a first preferred embodiment of the present invention.

Figure 4A:
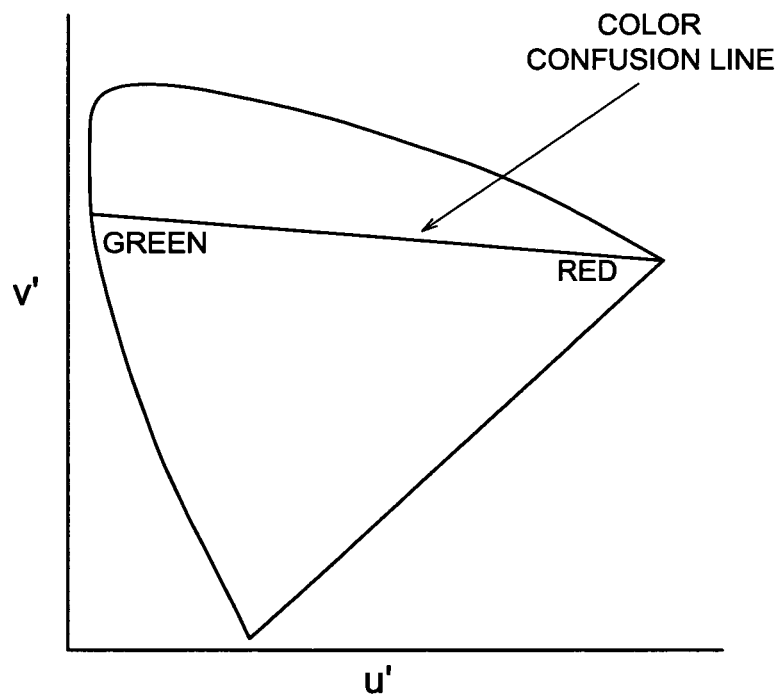
Figure 4B:
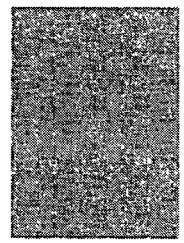
Figure 4C:
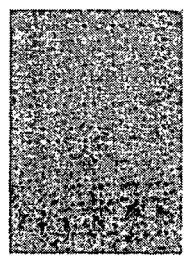
Figure 4D:
Figure 4E:

FIG. 4a is an explanatory diagram showing a chromaticity diagram and examples of applying textures in a first preferred embodiment of the present invention. FIG. 4b is an explanatory diagram showing a chromaticity diagram and examples of applying textures in a first preferred embodiment of the present invention. FIG. 4c is an explanatory diagram showing a chromaticity diagram and examples of applying textures in a first preferred embodiment of the present invention. FIG. 4d is an explanatory diagram showing a chromaticity diagram and examples of applying textures in a first preferred embodiment of the present invention. FIG. 4e is an explanatory diagram showing a chromaticity diagram and examples of applying textures in a first preferred embodiment of the present invention.

Figure 5:
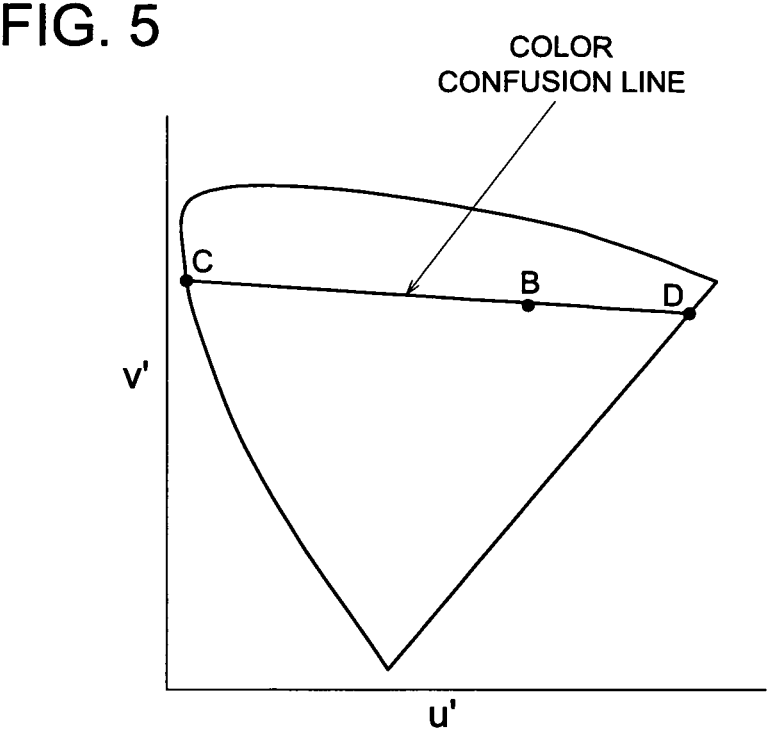

FIG. 5 is an explanatory diagram of the position in the chromaticity diagram in a first preferred embodiment of the present invention.

Figure 6:
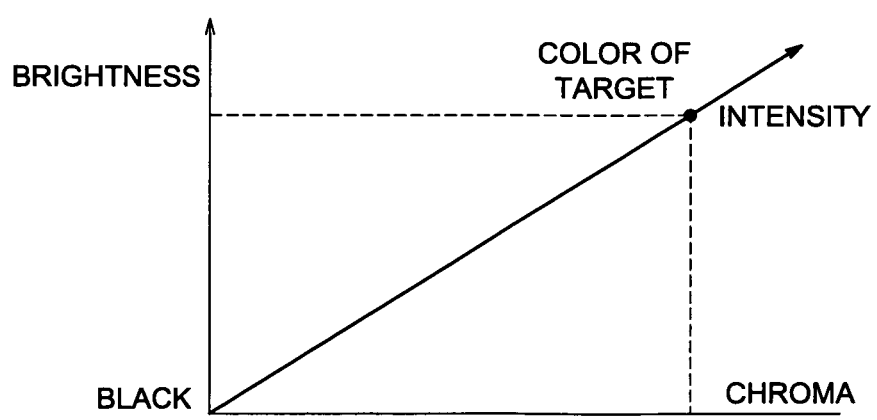

FIG. 6 is an explanatory diagram of the changes in the parameters in a first preferred embodiment of the present invention.

FIG. 7 is a block diagram showing the configuration of a first preferred embodiment of the present invention.

FIG. 8a is an explanatory diagram showing some examples of the duty ratios of hatching in a first preferred embodiment of the present invention. FIG. 8b is an explanatory diagram showing some examples of the duty ratios of hatching in a first preferred embodiment of the present invention. FIG. 8c is an explanatory diagram showing some examples of the duty ratios of hatching in a first preferred embodiment of the present invention.

FIG. 9a is an explanatory diagram showing some examples of the angles of hatching in a first preferred embodiment of the present invention. FIG. 9b is an explanatory diagram showing some examples of the angles of hatching in a first preferred embodiment of the present invention. FIG. 9c is an explanatory diagram showing some examples of the angles of hatching in a first preferred embodiment of the present invention.

FIG. 10 is an explanatory diagram explaining the form of color vision abnormality.

Figure 11A:
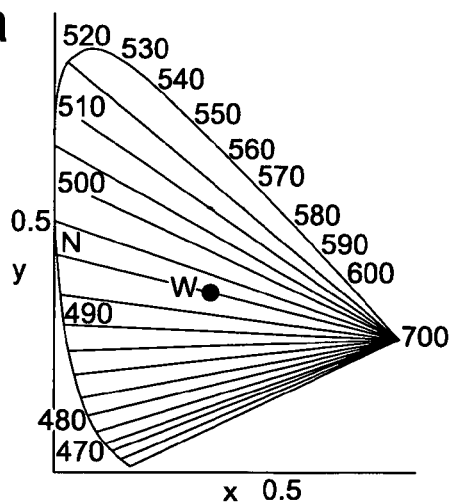
Figure 11B:
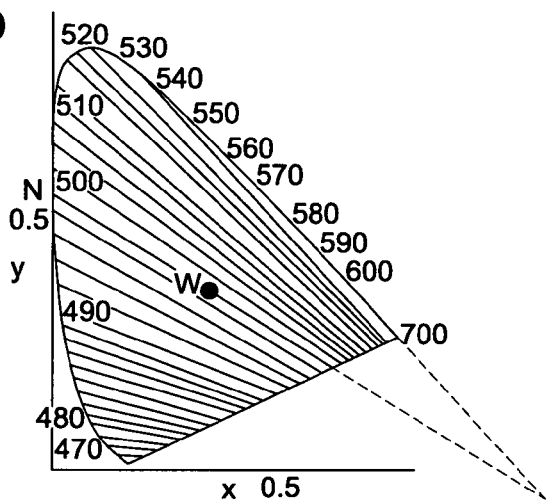
Figure 11C:
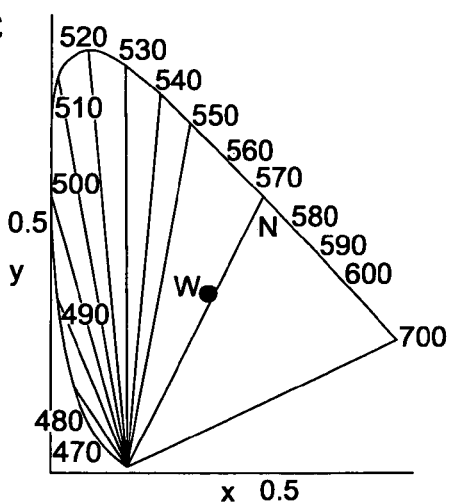

FIG. 11a is an explanatory diagram explaining the form of color vision abnormality. FIG. 11b is an explanatory diagram explaining the form of color vision abnormality. FIG. 11c is an explanatory diagram explaining the form of color vision abnormality.

Figure 12:
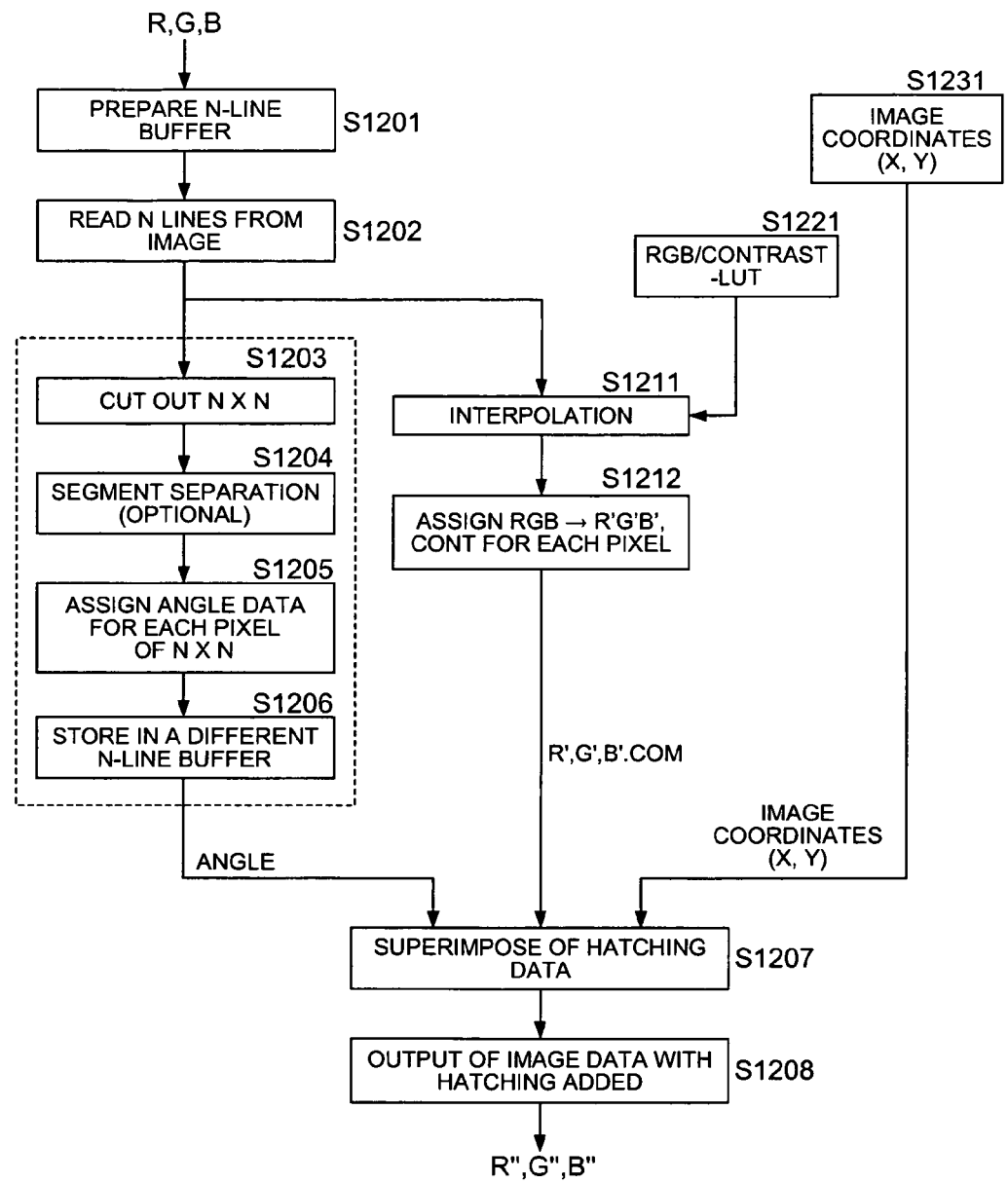

FIG. 12 is a flow chart showing the operation of a second preferred embodiment of the present invention.

Figure 13:
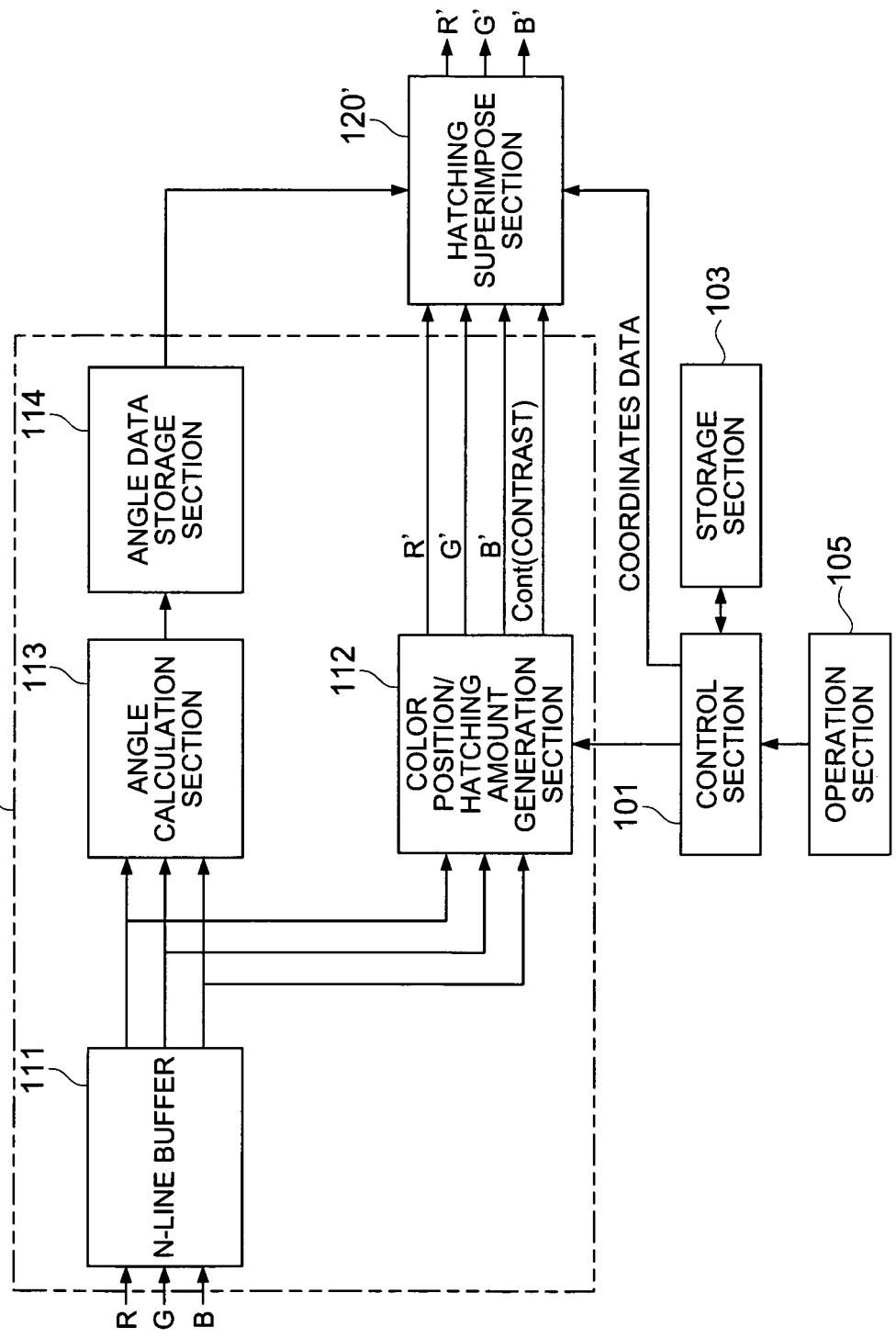

FIG. 13 is a block diagram showing the configuration of a second preferred embodiment of the present invention.

Figure 14:
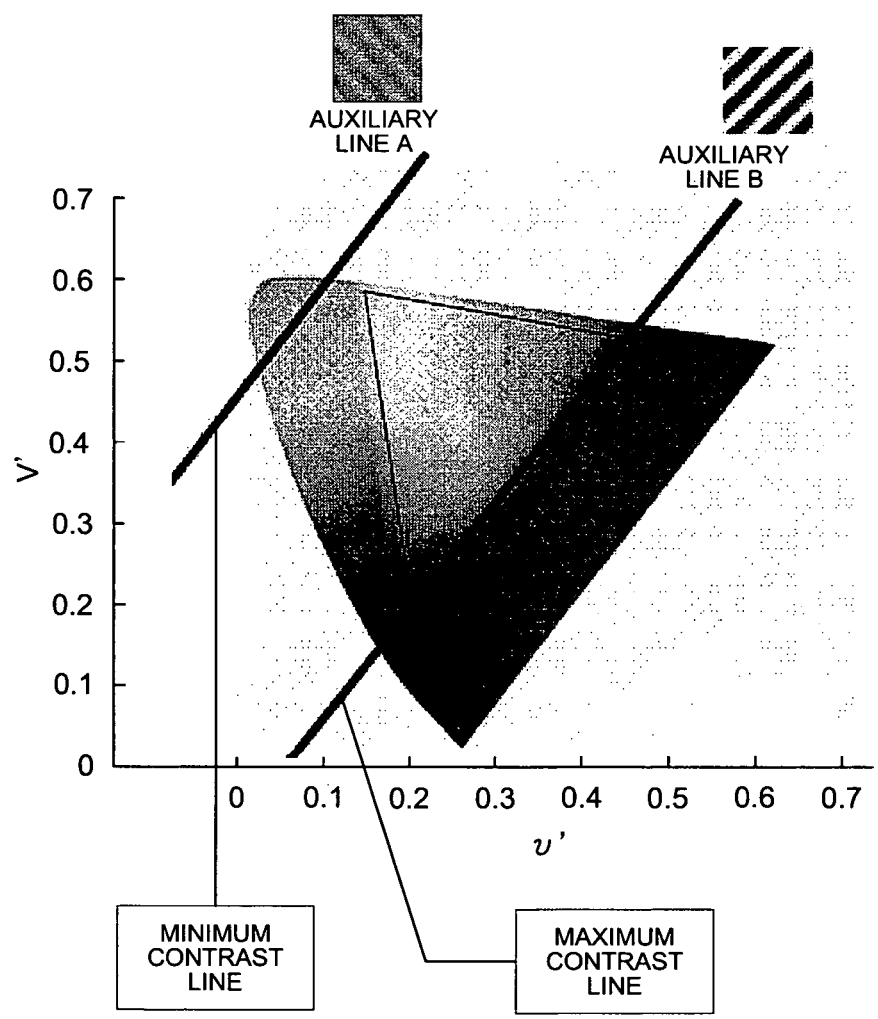

FIG. 14 is an explanatory diagram explaining a second preferred embodiment of the present invention.

Figure 15:
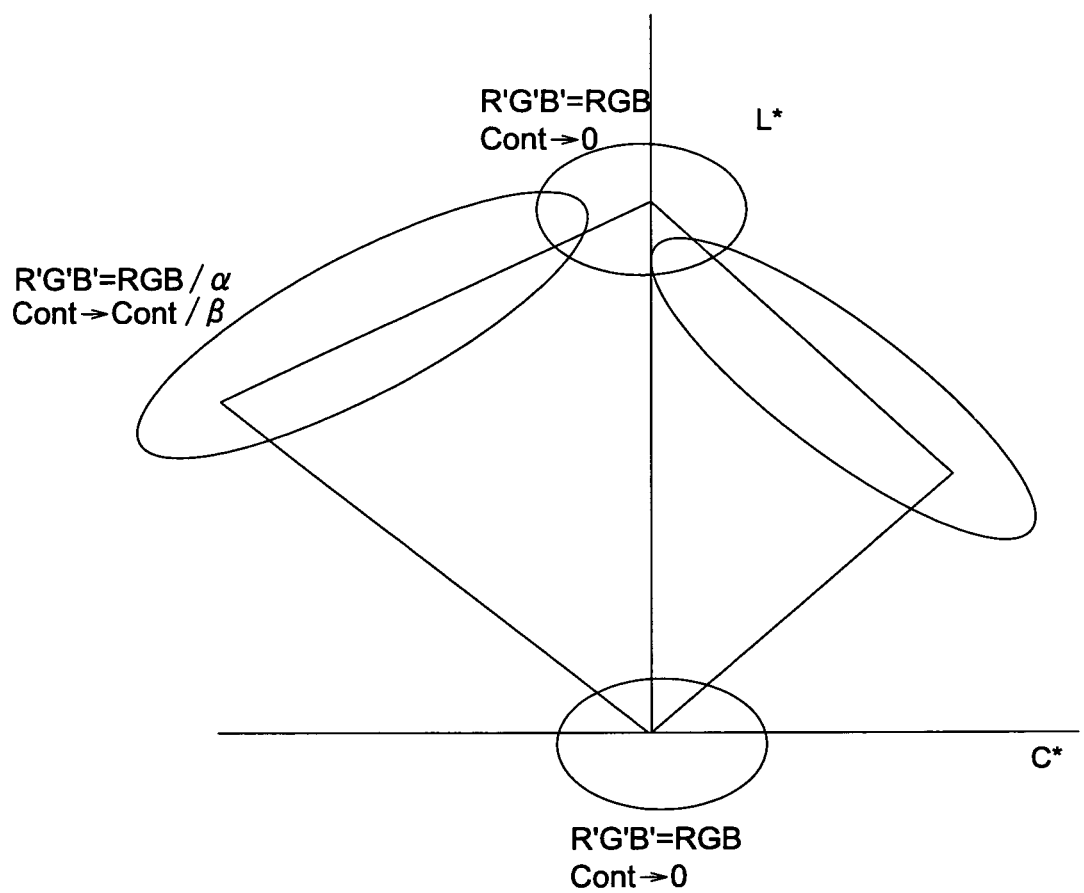

FIG. 15 is an explanatory diagram explaining a second preferred embodiment of the present invention.

Figure 16:
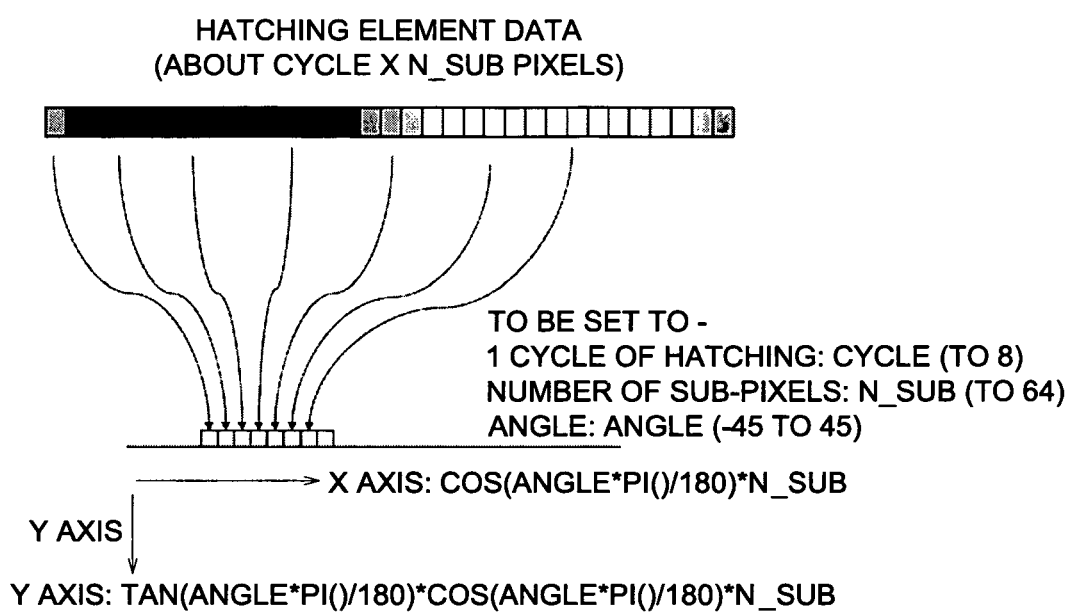

FIG. 16 is an explanatory diagram explaining a second preferred embodiment of the present invention.

Figure 17:
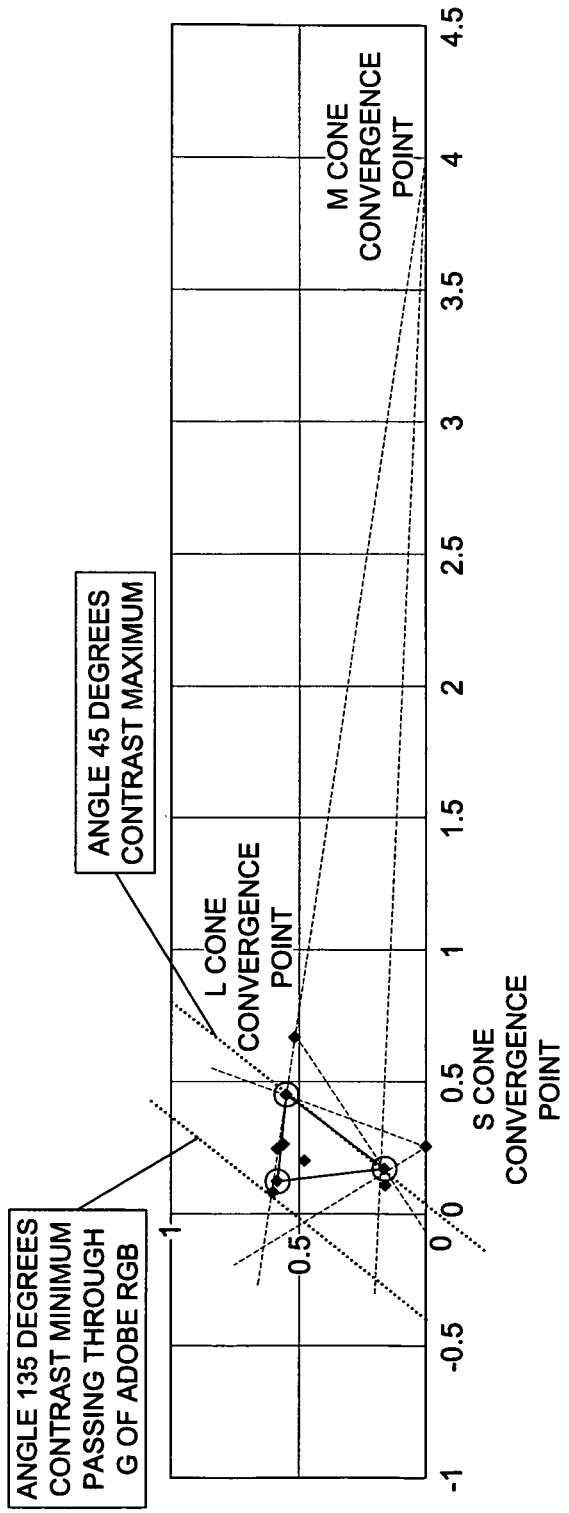

FIG. 17 is an explanatory diagram explaining a second preferred embodiment of the present invention.

Figure 18:
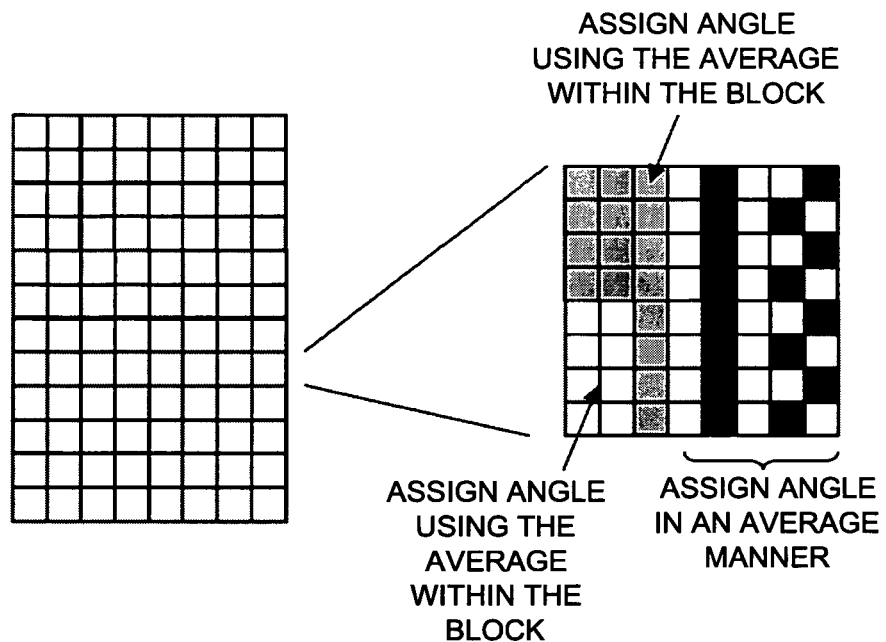

FIG. 18 is an explanatory diagram explaining a second preferred embodiment of the present invention.

Figure 19:
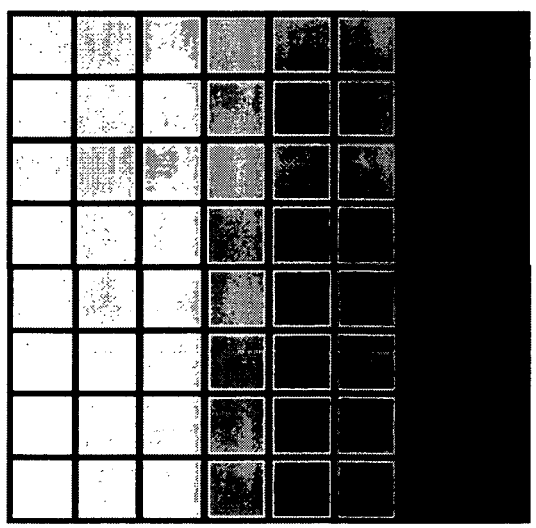

FIG. 19 is an explanatory diagram explaining a second preferred embodiment of the present invention.

Figure 20A:
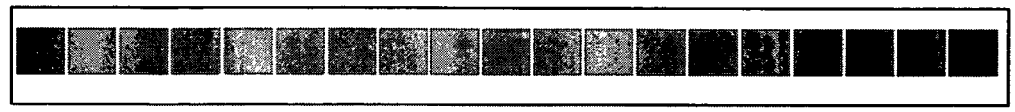
Figure 20B:
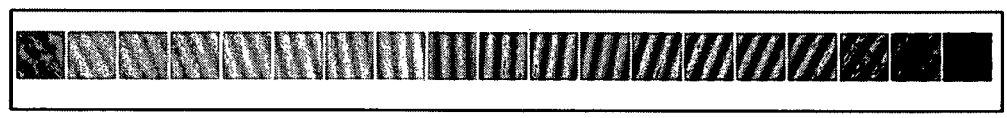

FIG. 20a is an explanatory diagram explaining a second preferred embodiment of the present invention. FIG. 20b is an explanatory diagram explaining a second preferred embodiment of the present invention.

Figure 21A:
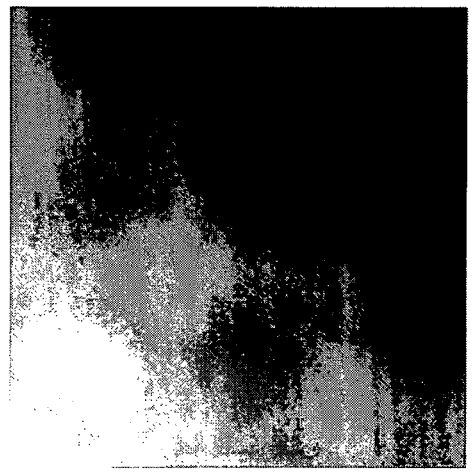
Figure 21B:
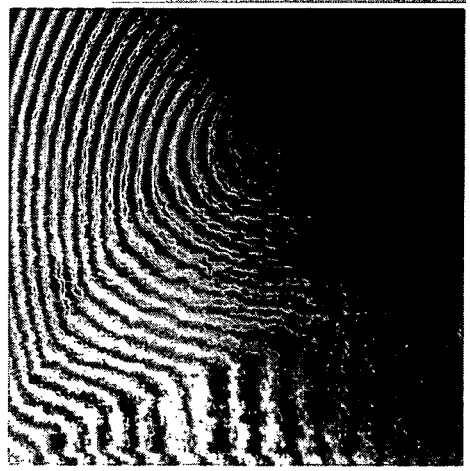

FIG. 21a is an explanatory diagram explaining a second preferred embodiment of the present invention. FIG. 21b is an explanatory diagram explaining a second preferred embodiment of the present invention.

Figure 22A:
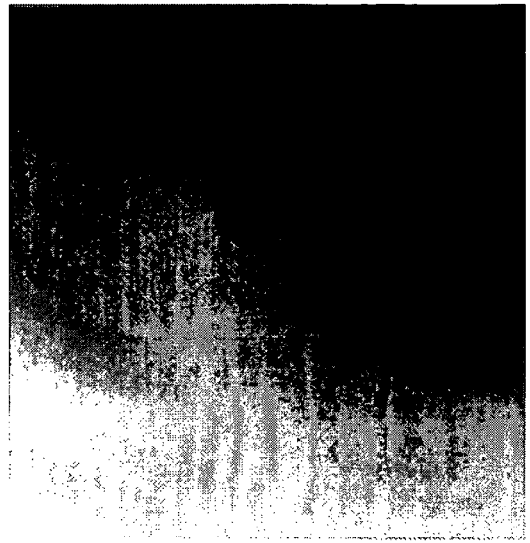
Figure 22B:
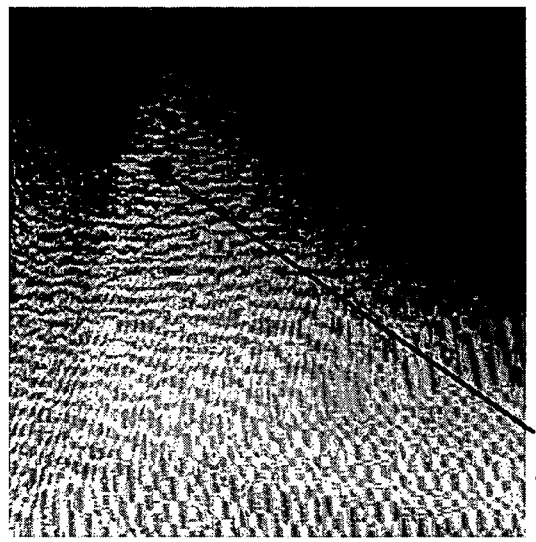

FIG. 22a is an explanatory diagram explaining a second preferred embodiment of the present invention. FIG. 22b is an explanatory diagram explaining a second preferred embodiment of the present invention.

Figure 23A:
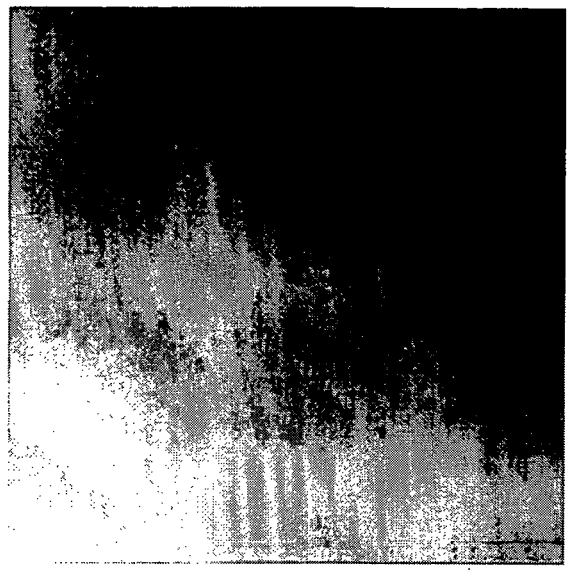
Figure 23B:
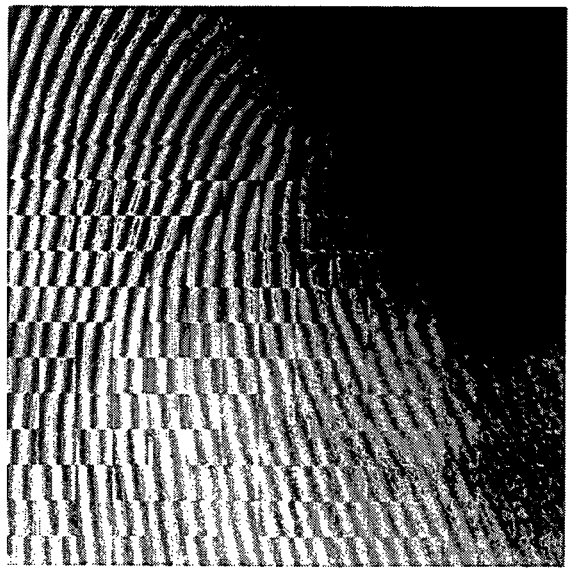

FIG. 23a is an explanatory diagram explaining a second preferred embodiment of the present invention. FIG. 23b is an explanatory diagram explaining a second preferred embodiment of the present invention.

FIG. 24a is an explanatory diagram explaining a second preferred embodiment of the present invention. FIG. 24b is an explanatory diagram explaining a second preferred embodiment of the present invention.

FIG. 25a is an explanatory diagram explaining a second preferred embodiment of the present invention. FIG. 25b is an explanatory diagram explaining a second preferred embodiment of the present invention.

Figure 26:
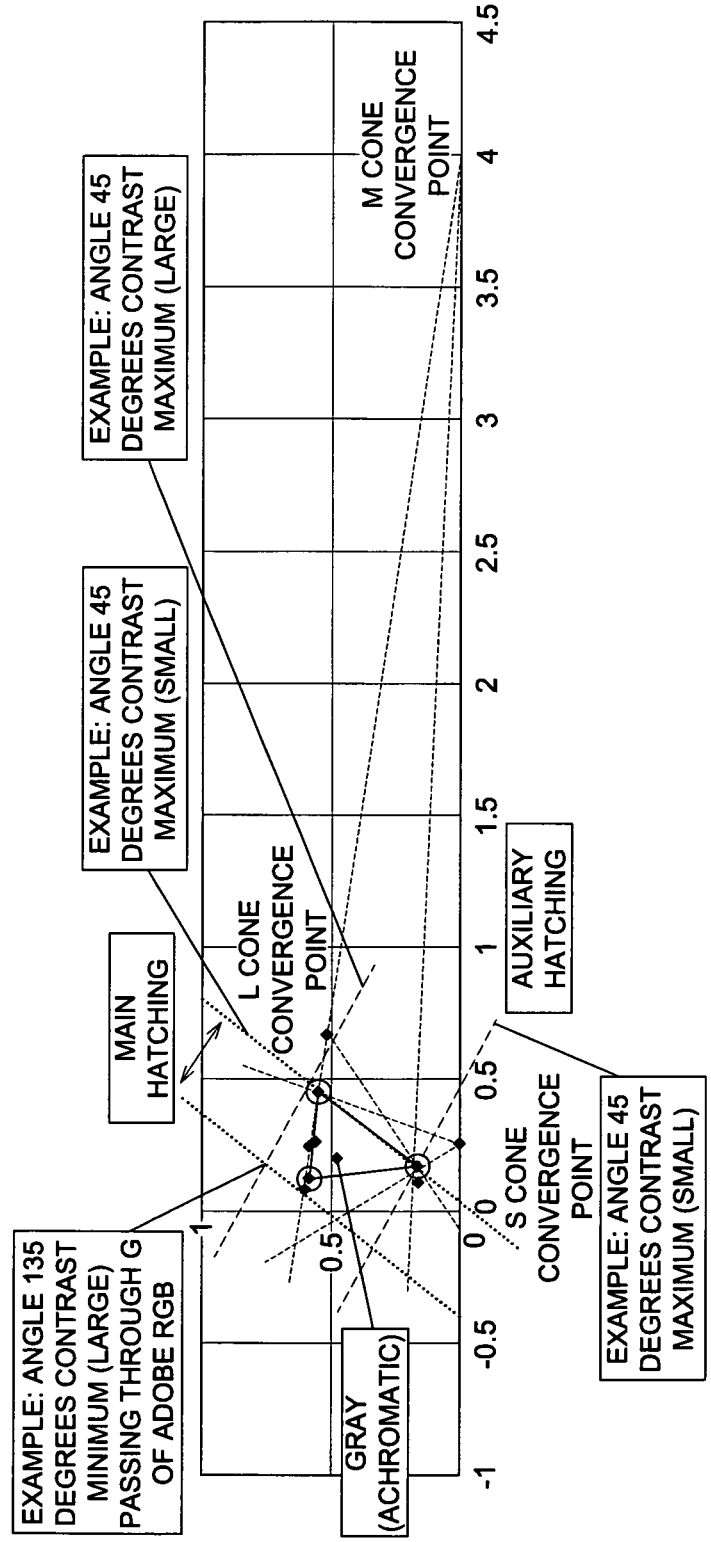

FIG. 26 is an explanatory diagram explaining a second preferred embodiment of the present invention.

Figure 27:
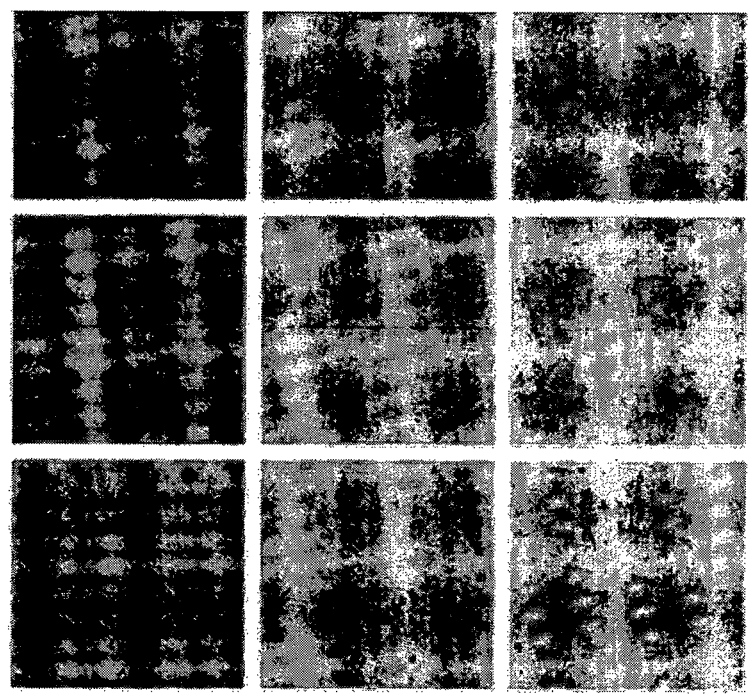

FIG. 27 is an explanatory diagram explaining a second preferred embodiment of the present invention.

DESCRIPTION OF SYMBOLS

100 Information conversion apparatus
101 Control section
103 Storage section
105 Operation section
110 Texture generating section
120 Image processing section

DETAILED DESCRIPTION OF THE PREFERRED EMBODIMENTS

Some preferred embodiments of the present invention are described in detail below with reference to the drawings.

Figure 2:
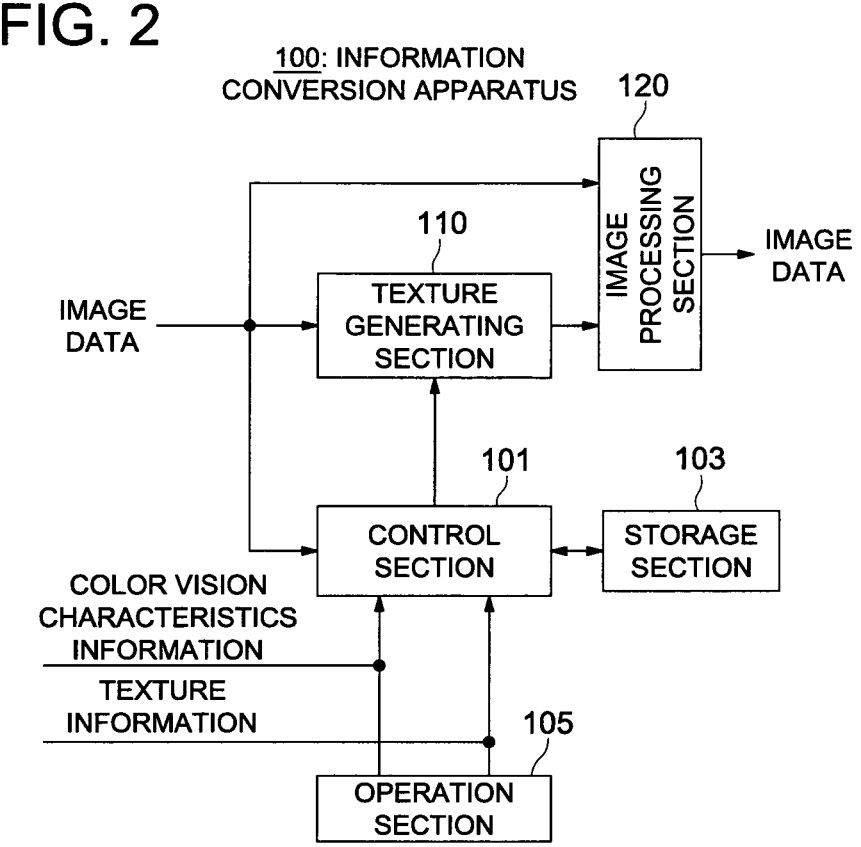
FIG. 2 is a block diagram showing the configuration of a first preferred embodiment of the present invention.

[A] First Preferred Embodiment (A1) Configuration of an Information Conversion Apparatus:

FIG. 2 is a block diagram showing the detailed configuration of an information conversion apparatus 100 according to a first preferred embodiment of the present invention.

However, the block diagram of the present information conversion apparatus 100 also expresses the processing procedure of the information conversion method, and the different routines of the information conversion program.

Further, in this FIG. 2, the items around the parts that are necessary for explaining the operation of the present preferred embodiment have been shown, and the other different types of items such as a power supply switch, power supply circuit, etc., that are well known as parts of an information conversion apparatus have been omitted.

The information conversion apparatus 100 according to the present preferred embodiment is configured so as to be provided with a control section 101 that carries out the controls for generating the textures according to the color vision characteristics, a storage section 103 that stores the information, etc., related to the color vision characteristics and the textures corresponding to them, an operation section 105 from which are input by the operator instructions related to the color vision characteristics information and the texture information, a texture generating section 110 that generates, according to the image data, the color vision characteristics information, and the texture information, various textures with different conditions according to the difference in the original colors regarding the regions on the color confusion line where, although the colors are different in the chromatic image the results of light reception are similar in the light receiving side and hence it is difficult to distinguish, and an image processing section 120 that synthesizes and outputs the textures generated by the texture generating section 110 and the original image data.

(A2) Procedure of the Information Conversion Method, Operation of the Information Conversion Apparatus, and Processing of the Information Conversion Program:

In the following, explanation of the operation of the present preferred embodiment is given referring to the flow chart of FIG. 1 and the characteristics diagrams of FIG. 3 and beyond.

Figure 1:
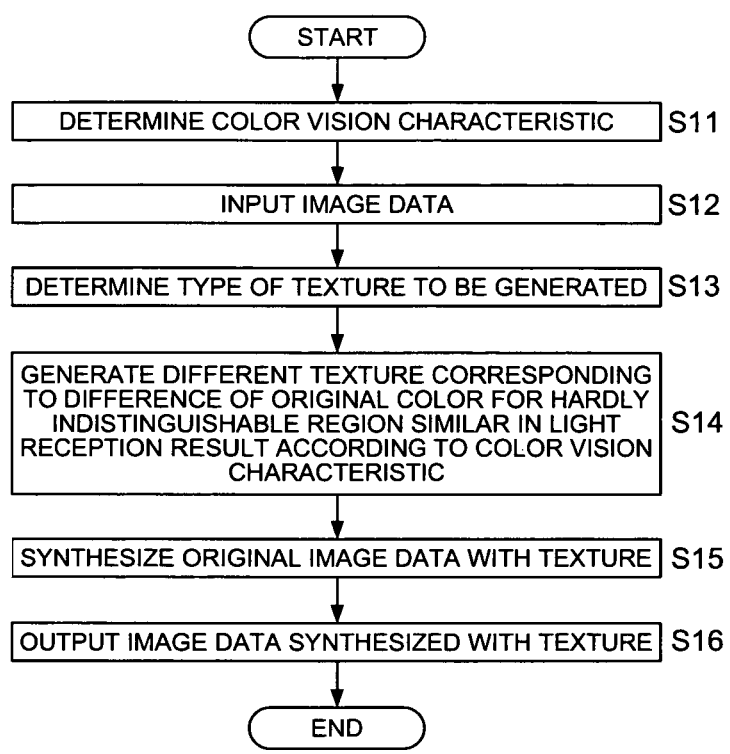
FIG. 1 is a flow chart showing the operation of a first preferred embodiment of the present invention.

Here, FIG. 1 shows the basic processing steps of the present preferred embodiment.

(A2-1) Determining the Color Vision Characteristics:

The color vision characteristics are determined that become the target at the time of carrying out information conversion of a color image according to the present preferred embodiment (Step S11 in FIG. 1). However, by making settings as described later, it is also possible not to carry out the step of determining the color vision characteristics but to set it in a fixed manner.

This color vision characteristics information is either input by the operator using the operation section 105, or is supplied from an external apparatus as the color vision characteristics information.

As this color vision characteristics information, if it is the case of a color vision abnormal person it can be the information as to which type the person belongs among the types shown in FIG. 10, or can be the information as to which color the person is not finding difficulty in distinguishing.

In other words, the information of color vision characteristics is the information related to the areas for which the colors are different in the chromatic image but the results of light reception at the light receiving side are similar (similar and difficult to distinguish).

(A2-2) Input of Image Data:

Next, the chromatic image data is input to the information conversion apparatus 100 (Step S12 in FIG. 1). However, it is also possible to provide an image memory not shown in the figure in the information conversion apparatus 100 and to store the image data temporarily.

(A2-3) Texture Determination:

Next, the control section 101 determines the type of textures to be added by carrying out information conversion regarding the color image according to the present preferred embodiment (Step S13 in FIG. 3).

This type of texture is determined by the texture information, and this texture information is either input by the operator via the operation section 105, or is supplied as texture information from an external apparatus. Or else, it is also possible for the control section 101 to determine the texture information according to the image data.

Here, a texture means the pattern in an image.

For example, a texture means spatial variation of color or density as is shown in FIG. 3a. However, here, although the expression has been made in monochrome due to the specifications of patent application drawings, in actual fact, this should be taken to mean spatial variation of color or density.

Further, a texture also means patterns of geometrical figures as is shown in FIG. 3b. However, here, although the expression has been made in monochrome due to the specifications of patent application drawings, in actual fact, this should be taken to imply geometrical figures in color.

Further, a texture also means hatching in the form of grid patterns as is shown in FIG. 3c. However, here, although the expression has been made in monochrome due to the specifications of patent application drawings, in actual fact, this should be taken to imply grid patterns in color. In addition, the composition of hatching need not only be 2-valued rectangular waveforms, but can also be smooth waveforms such as a sine wave.

(A2-4) Texture Generation:

Next, based on the instructions from the control section 101, the texture generating section 110, for the areas that have different colors in the chromatic image but the results of light reception in the light receiving side are similar and are difficult to distinguish, generates textures according to the differences in the original colors (Step S14 in FIG. 3).

Here, as is described later, regarding the areas, such as on a color confusion line, in which the results of light reception in the light receiving side are similar and are difficult to distinguish, according to the differences in the original colors, it is desirable to make the textures as textures having patterns or hatching with different angles, or textures having patterns or hatching with different contrasts, or textures that change such as blinking at different intervals, textures that move at different time periods, or at different speeds, or in different directions, or textures that move in different directions.

Further, even when the patterns are plain but they blink due to changes in the brightness, they are considered as textures in the present preferred embodiment.

Further, when the image data that is input is plain, it is possible to use any of the above textures.

In this case, if there is an instruction from the operation section 105 or from an external apparatus, textures are selected in accordance with that instruction. Further, if there is an instruction from the operation section 105 or from an external apparatus, the textures determined by the control section 101 are selected.

In addition, when hatching and patterns are present in the image data that is input, so as to differentiate from the existing hatching and patterns, the texture generating section 110 under instruction from the control section 101 generates textures of different types, or with different angles, or with different contrasts, or textures that change at different periods.

Here, it is assumed that the area in which the results of light reception on the light receiving side are similar and are difficult to distinguish is the color confusion line in the u'v' chromaticity diagram shown in FIG. 4a, and that the condition is one in which green to red is being found difficult to distinguish.

In this case, red before information conversion (FIG. 4b) and the green before information conversion (FIG. 4c) are in a condition in which it is difficult to distinguish between when viewed by a person with color vision abnormality.

In view of this, for example, in case hatching is selected as a texture, regarding the end part on the red side on the color confusion line, a hatching with an angle of 45 degrees is generated as the texture (FIG. 4d). Further, regarding the end part on the green side of the color confusion line, a hatching with an angle of 135 degrees is generated as the texture (FIG. 4e). Further, at positions in between the two end parts, hatching with continuously changing angles according to that position is generated as the texture.

Because of this, the condition is appropriate for viewing by a color vision abnormality person, and also, distinguishing is possible close to the original view equivalent to the viewing by a normal person.

Further, it is also desirable that the textures, according to the differences in the original colors, have different contrasts in the pattern or hatching of the texture. In this case, it is possible to make the contrast strong at one end on the color confusion line and the contrast weak at the other end, and to change the contrast continuously in between. In addition, it is also good to make the contrast weak at the middle and strong at the two ends.

Further, apart from the angle or contrast of the pattern or hatching, as the density of hatching (spatial frequency), it is possible to make it dense or closely packed at one end on the color confusion line and to make it sparse at the other end, and to change the density continuously. Even for this, it is possible to think of various methods for the setting of the denseness or sparseness of the frequency in a similar manner.

In addition, instead of the angle of the pattern or hatching, as the duty ratio of the pattern or hatching, it is also possible to change continuously the thickness of the hatching line according to the position on the color confusion line. Also, it is also possible to change the duty ratio according to the brightness of the color to be expressed.

Furthermore, this texture can also be made a combination of two or more of—pattern or hatching with different angles according to the difference between the original colors, with different contrasts according to the difference between the original colors, changing with time or moving at different speeds according to the difference between the original colors, and moving in different directions and with different speeds according to the difference between the original colors. In addition, even in this case, it is also possible to make the state differ roughly continuously according to the difference between the original colors. In this case, by changing a plurality of combinations, it is possible to express the position on the color confusion line freely.

Further, when not printing out but displaying in a display, etc., instead of the angle of hatching, as the speed of movement or direction of movement of hatching, by making it stop at the middle position on the color confusion line, making the speed of movement higher as one end is reached, and by making it move in the opposite direction with increasing speed as the other end is approached, it is possible to make continuous changes according ta the position on the color confusion line. In addition, even when other textures are used, it is possible to express the position on the color confusion line by the angle of that texture, duty ratio, speed of movement, blinking frequency, etc.

(A2-5) Synthesizing Textures:

Next, in the image processing section 120, the textures such as the above that are generated in the texture generating section 110 and the original image are synthesized (Step S15 in FIG. 1). Further, at this time, before and after adding the textures, it is desirable that no change occurs in the average color or average density of the image. For example, in the condition in which the textures have been added, dark colored hatchings are added in the base part of a lighter color than the color of the original image. In this manner, it is desirable that the observation by a normal person is not affected and the original view is retained by not changing the average color in the region in which a texture has been added from the original color, or by making it resemble the original color.

(A2-6) Outputting Converted Image:

The image after conversion by adding textures to the original image in this manner in the image processing section is output to an external apparatus such as a display device or an image forming apparatus (Step S16 in FIG. 1).

Further, the information conversion apparatus 100 according to the present preferred embodiment can exist independently, or can also be incorporated inside an existing image processing apparatus, or an image display apparatus, or in an image outputting apparatus. Further, when incorporated inside another apparatus, this can also be configured to use commonly the image processing section or the control section of that other apparatus.

(A3) Details of Information Conversion:

Although in the above, as a sequential flow, the information conversion method, apparatus, and processing of the program according to the present preferred embodiment were explained, the details such as the determination of parameters at that time, etc; are described below.

In the preferred embodiment described above, regarding areas such as on the color confusion line in which the results of light reception at the light receiving side are similar and difficult to distinguish, it is possible not to affect the observation by a normal person and to retain the original view and in a condition suitable for observation by a color vision abnormality person by adding textures, according to the difference in the original colors, such as textures including patterns or hatching with different angles, textures having patterns or hatching with different contrasts, textures that change, such as blinking at different periods, textures that move with different periods or speeds or in different directions, textures that move with different speeds or in different directions, or textures that are combinations of a plurality of these.

Here, the parameters of the type of texture are what pattern, or hatching, or angle, or contrast the texture has to have.

Further, the period of blinking of the texture, the duty ratio of blinking, the speed and direction of movement, etc., constitute the temporal parameters of the texture. It is possible to determine these parameters in the following manner.

(A3-1) Relative Position:

The temporal parameters (period, speed, etc.) at the time of changing the texture of the image or/and the parameters of the type of texture are determined to correspond to the relative position of the color of the object on the color confusion line.

Although the position naturally differs depending on the coordinate system such as RGB, or XYZ, the position can also be, for example, the position on the u'v' chromaticity diagram. Relative position is the position that is expressed as a ratio with respect to the overall length of the line.

When the color of the object to be converted is taken as the point B in the u'v' chromaticity diagram, the left end of the two points of intersection of the color confusion line passing through point B and the color region boundaries is taken as point C and the right end is taken as point D, the relative position P_b of point B can be expressed, for example, by the following equation (3-1-1). If a diagram is drawn, for example, that will have the positional relationships in the u'v' chromaticity diagram such as that shown in FIG. 5.

$$P\_b = BD/CD \quad (3\text{-}1\text{-}1)$$

As a method of actually expressing the position, it is also possible to express the position by increasing the reference points further apart from points C and D. For example, the point of achromaticity or the points of intersection with black body locus, point of simulation of color vision abnormality, etc, can be added as a new reference point, point E, and the relative position of the point B can be taken on the line segment CE or the line segment ED.

(A3-2) Parameter Change According to the Position:

Changing the temporal parameters (period, speed, etc.) or/and changing the parameter of the type of texture at the time of changing the texture of the image according to the position is obtaining, using the conversion function or the conversion table, from the position information such as the value of the equation (3-1-1), the temporal information (period, speed, etc.) at the time of changing the texture of the image or/and a part of the parameter of the type of texture. It is also possible to vary two or more parameters, and it is possible to increase the discrimination effect by making large the apparent change.

(A3-3) Continuity:

Although the above parameters can be continuous or non-continuous, it is desirable that they are continuous. When the change is continuous, in a condition suitable for observation by color vision abnormality persons, distinguishing becomes possible close to the original view equivalent to the observation by normal persons, colors can be grasped accurately, and even fine differences in the colors can be understood. However, in the case of digital processing, it will not be completely continuous.

(A3-4) Taking Ease of Distinguishing Close to that of Normal Persons:

It is desirable that the effect of ease of distinguishing by color vision abnormality persons as a result of parameter change correspond with the effect of ease of distinguishing by normal persons using the original colors. By making the ease of distinguishing resemble each other, the reading out the display becomes closer to that of a normal person. If the parameter change corresponding to the position is made a continuous change, the person observing can observe the fine changes in the color as changes in the parameters, and the ease of distinguishing becomes closer to that of a normal person. The color differences can be taken as a reference for the ease of distinguishing by a normal person using the original colors. For example, since FIG. 5 uses a uniform color space, it is sufficient to make the parameters change so that the ease of distinguishing by a color vision abnormality person changes in correspondence with the relative position on the color confusion line of FIG. 5.

(A3-5) Contrast of Textures:

Here, the contrast of textures is explained using a concrete example of parameter change. There is the method of changing the contrast of hatching as a parameter change of the temporal parameters (period, speed, etc.) or/and parameter change of the type of texture at the time of changing the texture of a concrete image. In this case, for example, the contrast Cont_b of the color of point B is obtained using Equation (3-5-1). This is the method of interpolating the contrast of the line segment CD taking as reference the contrast Cont_c of point C and the contrast Cont_d of the point D as the reference, and determining the contrast Cont_b according to the position of point B. Using this method, it is possible to assign a continuous parameter.

Equation 1:

$$Cont\_b = Cont\_c * BD/CD + Cont\_d * (1 - BD/CD) \quad (3\text{-}5\text{-}1)$$

For the unit of this contrast, it is desirable to use the color intensity difference. The color intensity is the length from the black point which is the origin to the target color, and is as shown in FIG. 6. For example, although the color of RGB=(1.0, 0.0, 0.0) and the color of RGB=(0.5, 0.0, 0.0) are both red with equal chromaticity, the color intensity of one is twice the color intensity of the other.

It is also possible to use a unit system in which the maximum value of the intensity differs depending on the chromaticity. For example, the three colors of the color of RGB=(1.0, 0.0, 0.0), the color of RGB=(0.0, 1.0, 0.0), and the color of RGB=(6.0, 0.0, 1.0) each have their respective maximum brightness, but is also possible that their intensity values are different so that their values are different. On the contrary, for all chromaticities, it is also possible to normalize so that the intensity becomes 1.0 at the condition of maximum brightness. It is desirable to make the intensity and brightness become equal in the achromatic condition.

In concrete terms, the intensity P can be expressed by Equation (3-5-2) or by the color of Equation (3-5-3).

Equation 2:

$$P(R, G, B) = \sqrt{\frac{aR^2 + bG^2 + cB^2}{a + b + c}} \quad (3\text{-}5\text{-}2)$$

Equation 3:

$$P(R, G, B) = \text{Max}(R, G, B) \quad (3\text{-}5\text{-}3)$$

Here, Equation (3-5-2) is an equation of intensity in which it is possible to change the maximum intensities of R, G, B, respectively can be changed by the ratios of the coefficients a, b, and c. Equation (3-5-3) is an equation of intensity in which the intensities have been normalized to be 1.0 at the maximum brightness.

(A3-6) Change of Temporal Parameters:

Here, concrete examples of parameter changes of temporal parameters are explained.

Although changing the period of blinking is a concrete example of the parameter change of temporal parameters (period, speed, etc.) at the time of changing the texture of an image, this does not easily contribute to the ease of distinguishing.

It is desirable that changes in temporal parameters are combined with changes in the texture. As in an electric sign board, by changing the time of characters and also changing the time of patterns, they become parameters that have effect on the ease of distinguishing. If the direction of flow of the pattern is taken as a parameter, the distinguishing becomes still easier. An effect similar to the parameter "angle of segmenting a region" described later will also be obtained.

(A3-7) Retention of Average Color:

As has already been explained, the average of all the colors displayed when the temporal parameters (period, speed, etc.) are changed at the time of changing the texture of the image or/and when the type of texture is changed is made roughly equal to the color of the image before conversion. For this averaging, although the method of simply adding up all the colors and dividing by the number of colors is simple, it is desirable to use an average considering the area, or an average considering the display duration, etc.

'Adding up' is that of light synthesis by additive mixing of colors either when the present preferred embodiment is applied to light emission displays such as display monitors or electrical sign boards, or when applied to printed matter such as paper, painted sign boards, etc.

'Roughly equal to' can mean either taking a color difference of 12 or less of the reference value which is taken as the same color system in JIS (JISZ8729-(1980)), or can be within a color difference of 20 or less of the reference value which is the management of color name levels given in page 290 of the New Color Science Handbook, 2nd edition.

For example, in the case of the method of hatching with two colors, if the areas of the two colors are equal, then it is sufficient to take a simple average of the two colors. If the color of the object is violet, if the hatching is of red and blue colors, then the average will be the violet color.

(A3-8) Retention of Chromaticity:

As has already been explained, the chromaticity of all the colors displayed when the temporal parameters (period, speed, etc.) are changed at the time of changing the texture of the image or when the type of texture is changed is made roughly equal to the chromaticity of the object before conversion. Although it is possible to change the chromaticity of the texture pattern, in this case, it becomes difficult to realize that it is a hatching because of the color vision characteristics of humans. This is because, in the color vision characteristics of humans, changes in darkness and brightness are more easily recognized than changes in the chromaticity. By unifying the chromaticity, it is possible to observe that it is a part constituting the same object, and also there is less feeling of discomfort. It is possible to convey without mistakes the chromaticity that leads to the judgment of color names.

In concrete terms, in the case of the method of hatching, since it is a change in the type of texture constituted by two straight lines (or areas of different colors), it is sufficient to make the respective chromaticities of the two lines roughly equal to each other, and to change only the intensities. Because of this, it is possible to share text with persons having normal color vision, and it is possible to obtain the effect that there is no mistaking of the chromaticity, there is small feeling of discomfort, and there is small, reduction in the effect of distinguishing at high frequencies.

(A3-9) Adjustment of Spatial Frequency:

Here, concrete examples of parameter change regarding the adjustment of spatial frequency are described.

The spatial frequency of the pattern of the texture used is changed according to the shape and size of the image. In other words, the frequency is set according to the size of the image to which the texture is applied and according to the size of the text characters contained in the image.

For example, if the spatial frequency of the pattern is low and it is not possible to recognize the periodicity within the image, the person viewing cannot recognize a pattern as a pattern, but may recognize it as a separate image. On the other hand, if the spatial frequency of the pattern viewed by the observer is high, it may not be possible to recognize the presence or absence of the pattern. In particular, as the distance from the observer to the display increases, the frequency viewed by the observer becomes high, and it becomes difficult to recognize the presence or absence of the pattern.

Therefore, in concrete terms, the lower limit of the frequency is set according to the overall size of the object, the upper limit of the frequency is set according to the overall text character size, and any frequency within those lower and upper limits are used.

Because of this, since the frequency is higher than the lower limit, the periodicity of the pattern in the object can be recognized, and since it becomes clear that the pattern is really a pattern, the pattern is not mistakenly recognized as an object. In addition, since very often the observer views the display from a distance at which the text characters can be read, there is the effect that the presence or absence of pattern can be recognized if the frequency is up to a high frequency of the same level as the text character size.

In this case, as is shown in FIG. 7, the object characteristics detection section 107 extracts the spatial frequency contained in the image, the text character size, the size of figure objects, etc., as the object characteristics information, and conveys them to the control section 101. Next, the control section 101 determines the spatial frequency of the texture according to the object characteristics.

(A3-9-1) Method of Determining the Spatial Frequency:

Further, the following is used and the method of determining the spatial frequency.

(A3-9-1-1) Basic Thinking:

The frequency of the object is avoided and the frequency is made higher or lower than that frequency. This is done in order to avoid confusion between the object and the hatching, and to cause the recognition of the presence or absence of hatching.

Further, the presence or absence of hatching cannot be recognized if the frequency is too high, and if the frequency is too low, there is the likelihood of confusion between the object and hatching.

(A3-9-1-2) In the Case of Text Characters:

When a person reads text, that person adjusts the distance according to the size of the text characters. From experiments it was found that people view at a distance so that the size of the text characters is about 0.2 degrees. Considering the spatial resolution of the eye and the spatial frequency of the structure of the text itself, it was found that a frequency of less than three times the frequency of the text character size is desirable. When the frequency is higher than this, there will be interference with the text characters making them difficult to view, and it may not be possible to recognize as hatching visually.

(A3-9-1-3) In the Case of Geometric Objects:

In the case of circular or rectangular objects, a frequency of more than twice or less than half is desirable. This is for avoiding confusion between geometric objects and hatching.

(A3-9-1-4) Modified Example:

Further, as a modified example, in case there are text characters and objects with different sizes, it is desirable to follow the above standard according to nearby text character sizes and objects, and to determine the nearby frequency in an adaptive manner.

(A3-10) Duty Ratio of Hatching or Patterns:

Here, concrete examples of parameter changes are explained regarding the duty ratios of hatching or patterns.

When the average color is a color near the color region boundary, in order to solve the problem that the contrast cannot be made high, the duty ratio of hatching of pattern is changed appropriately.

Although a constant value is normally used for the duty ratio in hatching, when hatching an object whose color is near the color region boundary, if the color difference is made higher than a certain value without changing the average color, sometimes a part of the color may cross the color region boundary. Because of this, it may not be possible to realize hatching with the above parameter.

In the above case, it is sufficient to increase appropriately the display of the color near the color region boundary while setting the contrast so that it does not cross the color region boundary. In the case of hatching, as is shown in FIGS. 8a, 8b, and 8c, it is sufficient to adjust the duty ratio appropriately. In the case of a wide spatial change, it is sufficient to increase the display using the area ratio, and to increase the display time if it is a temporal change. Because of this, it is possible to acquire color intensity difference without changing the average color.

For example, when generating hatching in black and white, near black, it is possible to set so that the area ratio is such that black>white.

(A3-11) Contour Line:

Contour lines are provided at the locations where hatching is used. By doing this, confusion between hatching and object is avoided. This can be used not only for hatching but also for other textures.

When using hatching, when the color of a neighboring object and the color of apart of hatching become roughly equal, depending on the shape of the neighboring image, it is possible that there is confusion between the two objects. In concrete terms, the slant lines constituting hatching are confused with the neighboring lines of the same color.

In the above case, contour lines are provided to the image for which hatching it used as the texture. It is desirable that the contour line is of the average color of the texture.

By doing this, the shape of the image becomes clear due to the contour line, and also, by making it of the average color, since the two colors of the slant lines of hatching and the contour line are different, it becomes difficult to confuse the image to which hatching is added and its neighboring image.

(A3-12) Angle of the Texture:

Here, concrete examples of parameter change are explained regarding the angle of the textures.

One of the parameters is taken as the angle of segmenting the region. By doing this, while it becomes easy to distinguish, in addition, in the case of angles, since the observer has an absolute reference, the chromaticity can be judged more accurately. If the correspondence between angle and chromaticity is determined in advance, it is easy to memorize the legend.

By changing the temporal parameters (period, speed, etc.) or/and by changing the type of texture at the time of changing the texture of a general image, since there is no standard for absolute judgment, it is difficult to read out said parameters. Since they are also difficult to keep in memory, it is difficult to establish correspondence between said parameters and the color without referring to the legend. It is better to express said parameters using a method by which it is easy to view as changes in shape, and an absolute judgment standard can be had.

Because of this, the angle of region segmentation is used as a parameter. In the case of the method of region segmentation, the parameter of the angle can be viewed easily as a change in the shape, and can be judged absolutely. In the case of concrete hatching, the angle Ang of point B under the conditions shown in FIG. 5 is determined by the following Equation (3-12-1). If the point B is taken as the center of the line CD, the angle Ang of the points BCD can be like any one of FIGS. 9a, 9b, and 9c.

$$Ang = 90 \times (BD/CD) + 45 \qquad (3\text{-}12\text{-}1)$$

Further, by making this angle change in the chromaticity diagram, it is possible to establish correspondence to some extent between the angle and the chromaticity. Since people have an absolute judgment standard for angles, it becomes easy to depend on memory, and it is easy to establish correspondence between said parameter and color without having to use the legend.

Concretely, in the case of first color vision abnormality, although it is common to confuse red, yellow, and green, because of the angle, it is possible to predict roughly that red is near the angle of 45 degrees, yellow is near the angle of 90 degrees, and green is near the angle of 135 degrees. If the correspondence is remembered, it is possible to judge to some extent the color without having to depend on the legend. Because of this, it also becomes easy to read out colors.

When this effect was experimented, for four normal persons under test, when one day had passed after showing the legend and the persons were asked to judge based on the angle, the error was about 60% compared to the case of not being able to judge based on the angle.

(A4) Others:

In the above preferred embodiment, although the color confusion line was taken as a concrete example of the region in which the results of light reception on the light receiving side were similar and could not be discriminated, it is not necessary to restrict to this. For example, it is possible to apply this similarly even when it is not the shape of a line but is a band or a region having a specific area in the chromaticity diagram.

In this manner, in the case of a region having a specific area, according to the two-dimensional position within that region, it is possible to take measures by assigning a plurality of parameters, such as angle and duty ratio of hatching.

Further, in the above preferred embodiment, by using as textures, according to the difference in the original colors, textures including patterns or hatching with different angles, textures having patterns or hatching with different contrasts, textures that change with time such as blinking at different periods, textures that move with different periods or speeds or in different directions, textures that move with different speeds or in different directions, distinguishing close to the original view equivalent to the observation by normal persons becomes possible in a condition suitable for observation by a color vision abnormality person.

Further, this type of effect can also be used when a normal person or camera observes or photographs images under a light source have a special spectral distribution. In concrete terms, when there is a light source having two types of single color lights, it is only possible to see colors that connect to those chromaticity points in the chromaticity diagram. For other directions, by adding textures indicated in the present invention, it is possible distinguish the colors.

In the preferred embodiment described above, as textures, it is not only possible to use patterns, hatching, or, contrast, angle, blinking, etc., of the patterns or hatching, but also, in the case of printed matter, etc., it is possible to include touch feeling realizing projections and depressions. Because of this, according to the differences in the original colors, distinguishing close to the original view equivalent to the observation by normal persons becomes possible in a condition suitable for observation by color vision abnormality persons. In this case, if it is a display device, it is possible to realize by forming or changing the projections and depressions by the extent of projection of a plurality of pins, or in the case of printed matter, it is possible to realize smoothness or roughness using paints.

Further, although the above explanations were of concrete examples of making distinguishing easy by adding textures to color regions that are difficult to distinguish in a chromatic image, the above preferred embodiment can also be applied to colors that are difficult to distinguish in achromatic colors (gray scale), or for colors that are difficult to distinguish in dark and light colors in a single color monochromatic image, and it is possible to obtain the good making distinguishing easy.

[B] Second Preferred Embodiment (B1) Configuration of an Information Conversion Apparatus:

FIG. 12 is a flow chart showing the operations (the procedure of execution of the information conversion method) of an information conversion apparatus 100 according to a second preferred embodiment of the present invention and FIG. 13 is a block diagram showing the detailed configuration inside an information conversion apparatus 100 according to a second preferred embodiment of the present invention.

In this second preferred embodiment, in order to visually recognize the angle of hatching, etc., considering that an area equal to at least one cycle of slant lines is necessary, the image is divided into prescribed areas, and the hatching angle is determined for each typical value of the pixel value (color) of those areas. Because of this, since an area is present, there is the feature that visual recognition of the hatching angle inside that area becomes improved.

Further, although the following second preferred embodiment uses hatching as a concrete example of a texture, and concrete examples are described in which the hatching angle is determined for each of the prescribed areas, it is possible to apply this to the first preferred embodiment described above. Therefore, duplicate explanations are omitted for the parts that are common to the first preferred embodiment described above, and explanations are given mainly for the parts that are different from the first preferred embodiment.

Further, in the block diagram of this information conversion apparatus 100, descriptions have been made centering on the surroundings of the parts that are necessary for explaining the operation of the present preferred embodiment, and explanations have been omitted for various known parts such as the power supply switch, power supply circuit, etc. as in other information conversion apparatuses 100.

The information conversion apparatus 100 according to the present preferred embodiment is configured to have a control section 101 that executes the control for generating textures according to the color vision characteristics, a storage section 103 that stores the information, etc., related to the color vision characteristics and the textures corresponding to them, an operation section 105 from which are input by the operator instructions related to the color vision characteristics information and the texture information, a texture generating section 110' that generates, according to the image data, the color vision characteristics information, and the texture information, various textures with different conditions according to the difference in the original color regarding the regions on the color confusion line where, although the colors are different in the chromatic image the results of light reception are similar in the light receiving side and hence it is difficult to distinguish, and an image processing section 120 that synthesizes and outputs the textures generated by the texture generating section 110' and the original image data.

Further, here, the texture generating section 110' is configured to be provided with an N-line buffer 111, a color position/hatching amount generation section 112, an angle calculation section 113, and an angle data storage section 114.

(B2) Procedure of the Information Conversion Method, Operation of the Information Conversion Apparatus, and Processing of the Information Conversion Program:

In the following, explanation of the operation of the present preferred embodiment is given referring to the flow chart of FIG. 12, the block diagram of FIG. 13, and the different types of diagrams of FIG. 14 and beyond.

(B2-1) Image Area Segmentation:

To begin with, the N-line buffer is prepared (Step S1201 in FIG. 12), and every N line of the RGB image data from an external apparatus is stored each time in that N-line buffer (Step S1202 in FIG. 12).

Here, at the time of adding textures of different angles corresponding to the differences in the original colors, the image data is segmented into areas configured from a plurality of pixels set in advance.

Although the method of segmenting this area depends on the resolution, it is desirable to segment in terms of every 8×8 to 128×128 pixels. This size becomes about 2 cycles/degree under standard observation conditions, and also, any power of 2 is desirable in order to make digital processing efficient.

Because of this, when the image is changing gradually, although the gradations are shown discretely, since the same angle is maintained as hatching within the same area, angles can be viewed accurately, and as a result, this leads to improvement in the ability to judge and recognize angles.

(B2-2) Calculation of Typical Value in the Area:

As described above, the area is segmented, and in the angle calculation section 113, N pixels×N pixels are cut out (Step S1203 in FIG. 12), and the typical value is calculated for each of those areas.

As this typical value calculation, in order to carry it out easily, it is sufficient to take the average using the signal values of each pixel within the area. Further, it can also be a middle value or some other value.

Further, this area of N×N pixels can also be resolved further in terms of the color distribution. In this case, the resolving is done in terms of a plurality of areas (segments) and the typical value for each of those segments is obtained. Because of this, in case the boundary of the image (the border part of color change) lies within a predetermined area, it is possible to make it a beautiful hatching without any artifacts. A general method of segmentation is used for resolving the areas.

(B2-3) Hatching Parameter Calculation:

Next, the hatching parameter (angle/contrast) corresponding to the above typical value is obtained. Refer to FIG. 14 here.

In a uniform chromaticity diagram shown in FIG. 14 (for example, the u'v' chromaticity diagram), a line that is almost perpendicular to the color confusion line and that is also an auxiliary line that passes through the end of the color region is drawn (can be a straight line, a piecewise linear line, or a curved line). For example, the angle and contrast are made maximum on the auxiliary line B that passes through red and blue, and the angle and contrast are made minimum on the auxiliary line A that passes through green.

Further, in the angle calculation section 113 of the present second preferred embodiment, the hatching parameter, angle, is determined based on the above auxiliary line A and the auxiliary line B. For example, the hatching angle is made equal to 45 degrees on the auxiliary line B passing through red and blue, and the hatching angle is made equal to 135 degrees on the auxiliary line A passing through green. In the first preferred embodiment described above, since the determination was made from the boundary line of color region, in part, there were locations where there was sudden change. However, the triangle shown in the figure is an sRGB area, and green is passing approximately through the fundamental color green of AdobeRGB (a trademark or a registered trademark of Adobe Systems Inc. in USA and in other countries, same hereinafter).

(B2-4) Determining the Contrast Intensity:

Here, the color position/hatching amount generation section 112 determines the intensity of contrast. Here, explanation is given referring to FIG. 15 (Step S1212 in FIG. 12). Further, here, the calculation is made not for the above described N×N pixels but for each pixel.

Although as a rule the relationship is made proportional to the angle, at the color region boundary where there is no margin in the intensity direction, either the contrast intensity is made weak or the brightness of the original color is adjusted.

This is because, otherwise, when contrast is added to the original color, the pixel value will become saturated.

Near white or near black of the horizontal axis C*=0 in FIG. 15, since the likelihood of wrong recognition is low even without hatching, the contrast is weakened and made 0. In other words, R'G'B' is made equal to RGB and Cont is made 0.

Further, in the part where the brightness L* is high excepting at C*=0, the intensity can be adjusted so that the target color is within the color region, and also, the contrast can be made weak. In other words, R'G'B' is made equal to RGB/α and Cont is made equal to Cont/β.

(B2-5) Image Processing (Hatching Superimposition):

According to the parameters determined as above, in the hatching superimpose section 120', the hatching is superimposed. Here, explanations are given referring to FIG. 16.

Here, the elements constituting hatching image are taken in advance in one line. Even the information of sub-pixels is also recorded in this hatching element. This is called the hatching element data.

Based on the X axis value and the Y axis value at which hatching is to be superimposed, the data of an appropriate location is called from the hatching element data. In other words, hatching is generated by carrying out prescribed sampling from a sine curve. This is made dependent on the X coordinate, the Y coordinate, and the angle. It is good to use the following equations for calculation which have also been shown in FIG. 16. As a modified example, the part of the trigonometric functions can be calculated in advance and can be put in the form of a table, thereby making it possible to carry out the calculations at a high speed.

X axis: $COS(Angle \times \pi/180) \times N\_SUB$

Y axis: $TAN(Angle \times \pi/180) \times COS(Angle \times \pi/180) \times N\_SUB$ 1 Period of hatching: CYCLE (to 8)
Number of sub-pixels: N_SUB (to 64)
Angle: Angle (−45 to 45)

However, this is assuming that the angle is taken to be 0 degree in the negative direction of the Y axis (upward direction) and that the angle is taken to increase as rotation is made in towards the right, and matching with the other preferred embodiments, if the angle is taken to be 0 degree in the positive direction of the X axis (towards the right) and the angle is taken to increase as rotation is made towards the left, the equations for the X axis and the Y axis become interchanged, that is, they will be as follows.

X axis: $TAN(Angle \times \pi/180) \times COS(Angle \times \pi/180) \times N\_SUB$ Y axis: $COS(Angle \times \pi/180) \times N\_SUB$ 1 Period of hatching: CYCLE (to 8)
Number of sub-pixels: N_SUB (to 64)
Angle: Angle (45 to 135)

Based on the above equations, which data among the array of hatching element data is to be sampled is determined, that is, the array element number is determined according to the following equation, and the hatching superimposition is carried out.

Array element number: $(P\_X \times X \text{ axis} + P\_Y \times Y \text{ axis})$ % $(CYCLE \times N\_SUB)$ X coordinate in the image: P_X
Y coordinate in the image: P_Y
Hatching element data array length: (CYCLE×N_SUB)

In other words, in the hatching superimpose section 120', the hatching information read out as above is superimposed on the pixel value according to the contrast intensity, thereby obtaining the new image data (Step S1207 in FIG. 12).

(B-6) Modified Example:

In the above processing, as a noise countermeasure, it is desirable that a low pass filter is applied to the chroma component thereby determining the contrast intensity.

Further, it is possible to change the intensity of the original color so that the difference can be understood slightly more, and thereafter if this method is applied, although the chromaticity is retained, the color vision abnormality persons can be made to recognize using the difference in intensity.

(B-7) Effect of the Preferred Embodiment:

(B-7-1) Setting the Chromaticity and Angle:

As the present second preferred embodiment, for example, red and blue=hatching of 45 degrees, gray (achromatic)=hatching of 90 degrees, and green=hatching of 135 degrees is determined.

By doing so, since gray becomes a vertically upward angle (90 degrees), there is the advantage that it is easy to remember the correspondence with the colors.

Here, as is shown in FIG. 17, the angle of coverage of the range of the color region from the convergence point of the color confusion line has been set so as to avoid the respective angles of the color confusion lines of the first color vision abnormality persons, the second color vision abnormality persons, and the third color vision abnormality persons. In other words, on the color confusion line of any color vision abnormality persons, the change in the hatching angle has been made to be observed. Because of this, it has been made possible to be distinguished by all of the color vision abnormality persons.

Further, in this example, since gray has been set as the middle point, it is convenient to assume the green of AdobeRGB for green. Because of this, at the same time, it also becomes possible to correspond to the colors of a broader color region.

Further, as is described later, targeting fully color blind persons who can only recognize brightness, it is also possible to superimpose auxiliary hatching in the range of −45 degrees to +45 degrees. Because of this, it becomes possible to correspond to all types of color vision abnormality persons.

(B-7-2) Correspondence to Gradation/Noise/Dither Images "Setting of Segmentation"

When the color has changed within the same grid area, it is judged as a plurality of colors as follows.

This algorithm is as follows.

Similar colors within the same area (for example, up to a difference of 5 in digital values) are present at the top, bottom, left and right, and the number of their connections is more than the number of pixels constituting the area, they are considered as segments, and an average color is assigned from all the pixels constituting it. The pixels that do not satisfy this are handled as exceptions, all the points of exception within a square block are collected together, and a comprehensive average color is assigned. Further, as is shown in FIG. 18, if the pattern is a checkered pattern due to dither, etc., or if it is simple vertical or horizontal pattern, since it appears visually as an average color, it has not been treated as a segment.

Further, because of handing this type of segments, hatching is done according to different colors neatly in the case of bar graphs, etc., and in the case of gradations such as in FIG. 19, the hatching is done with the average inside the grid (within square blocks).

(B-7-9) Verification of Effects:

A concrete example of determining the hatching angle for each area of a prescribed number of pixels according to the above second preferred embodiment is explained while referring to the drawings.

Further, although the original is a color printed matter, at the time of making the patent application, it has been read out in monochrome at the time that it was attached to the present patent application. In view of this, explanations in text are being added for the colors in the different drawings.

FIG. 20*a*, from left to right, shows 19 color samples that change gradually from green to red. FIG. 20*b*, from left to right, shows 19 color samples that change gradually from green to red with hatching added according to the present preferred embodiment.

In FIG. 21*a* is an image in which the color is changing gradually (chromatic) so that top left is magenta and bottom right is green, and also, gray (density of achromatic color) is changing gradually so that top right is black and bottom left is white.

FIG. 21*b* is an image which is the image of FIG. 21*a* to which is added hatching in units of one pixel by calculating the angle in units of 1 pixel, and shows the generation of moire pattern phenomenon, and it can be seen that there is a hatching angle other than the expected one at gray (should have been a hatching angle of 90 degrees) and green (should have been a hatching angle of 120 degrees). Further, within the green region, there are areas in which there is a sudden change in the hatching angle that is not intended.

FIG. 22*a* is an image in which the color (chromatic) is changing gradually so that top left is red and bottom right is cyan, and gray (density of achromatic color) is changing gradually so that top right is black and bottom left is white.

FIG. 22*b* is an image which is the image of FIG. 22*a* to which is added hatching in units of one pixel by calculating the angle in units of 1 pixel, and shows the generation of moire pattern phenomenon, and it can be seen that there is a state of a hatching angle other than the intended one at red (should have been a hatching angle of about 45 degrees to 60 degrees) (at the position indicated by the arrow in the figure).

FIG. 23*a* is similar to FIG. 21*a*, and is an image in which the color is changing gradually (chromatic) so that top left is magenta and bottom right is green, and also, gray (density of achromatic color) is changing gradually so that top right is black and bottom left is white.

FIG. 23*b* is an image which is the image of FIG. 23*a* to which is added hatching with the angle calculated for areas in units of sixteen pixels, and the hatching is at an angle of 90 degrees for gray, the hatching angle is about 120 degrees for green, and the hatching angle is about 60 degrees for magenta, and can be viewed with the desired hatching angles. Further, there is no sudden change in the hatching angle.

FIG. 24*a* is similar to FIG. 22*a*, and is an image in which the color (chromatic) is changing gradually so that top left is red and bottom right is cyan, and gray (density of achromatic color) is changing gradually so that top right is black and bottom left is white.

FIG. 24*b* is an image which is the image of FIG. 24*a* to which is added hatching with the angle calculated for areas in units of sixteen pixels, and the hatching is at an angle of 90 degrees for gray, the hatching angle is about 45 degrees for red, and the hatching angle is about 120 degrees for cyan, and can be viewed with the desired hatching angles. Further, there is no sudden change in the hatching angle.

Further, after carrying out experiments with various types of images not shown here in the figures, it was clear that it could be seen in the condition in which hatching was added to the image similar to the hatching angles for the color samples shown in FIG. 20.

Further, according to the processing of segments described above, when joints of hatching occur within the prescribed areas as shown in FIG. 25*a*, it is possible to make the hatching without the joints of hatching such as shown in FIG. 25*b*. Because of this, it was confirmed that the degree of visual recognition increased further due to the angle of hatching.

[C] Third Preferred Embodiment:

In the above first preferred embodiment and the second preferred embodiment, textures such as hatching were added to color images, thereby making it possible for both normal color vision persons and persons with color vision abnormality to recognize the differences in color.

In contrast with this, in the present third preferred embodiment, at the time of printing out color original document or color image data by monochrome printing, the feature is that the above first preferred embodiment and the second preferred embodiment are applied.

In other words, the final monochrome image is formed by adding hatchings of different angles according to the differences in the colors. Because of this, the problem of distinction between colors being unable to be made during monochrome printing will be solved. In this case, it is possible to realize the above by incorporating the circuit or program implementing the above preferred embodiments in the computer, or printer, or copying machine.

Because of this, it is possible to contribute to resource saving because it is possible to use monochrome printers efficiently, or, because the use of expensive color inks or color toners in color printers can be reduced.

Further, it is also possible to apply this third preferred embodiment to monochrome electronic papers that are coming into use in recent years such as displays with storage function using e-ink etc.

Further, in color printers, there is the advantage that printing can be continued even when the color into is exhausted, or when only black ink or black toner is remaining.

Further, in color printers, even when one of the color inks or color toners has been exhausted, there is the advantage that printing can be continued even in the condition in which that color is not used by making that color to be recognized by the angle of the hatching.

Further, at the time of carrying out this monochrome printing, in addition to the hatching in one direction (the main hatching) of the above preferred embodiment, it is desirable that a hatching (an auxiliary hatching) is added by calculating the hatching angle in a direction that is roughly at right angles to it (see FIG. 26).

The hatching is formed on the image by superimposing this auxiliary hatching along with the main hatching. Because of this, it will be possible to distinguish between different colors even with monochrome printing or even for fully color blind persons.

At this time, in order to distinguish between auxiliary hatching and main hatching, the frequency and angle are made different in the auxiliary hatching compared to that in the main hatching.

It is desirable to make,

Main hatching: 45 to 135 degrees,

Auxiliary hatching: −45 to 45 degrees (or −30 to 30 degrees, in order to avoid overlapping).

In addition, in the auxiliary hatching, it is desirable that the frequency is made higher than in the main hatching, thereby making it thinner. Desirably, a frequency of twice the frequency in the main hatching is good. Because of this, it is possible to distinguish between the types of hatching.

Further, in the case of gray, it is desirable that the main hatching is made vertical while the auxiliary hatching is made horizontal in order to make the discrimination of colors easier.

Further, there are several patterns regarding the hatching intensity, with the following four combinations that can be thought of—

Main hatching: (1) Green being made strong, red being made weak. (2) The reverse of this.

Auxiliary hatching: (A) Blue being made strong, red being made weak. (B) The reverse of this.

And (2) (B) or (1) (a) is desirable.

Since normal color vision persons use red as the color of importance, by making this kind of selection, it is possible to indicate even to persons with color vision abnormality the part with high hatching intensity, that is, as the color of importance. This selection, if the angle is fixed, and is appropriately changed depending on the type of image or the intentions of the document, it is possible to share between normal color vision persons and persons with color vision abnormality without error in discrimination between actual colors, and also, with the color of importance being recognized.

Further, as the hatching intensity, it is good to take zero as near gray, and to increase the hatching intensity according to the distance from gray, for example, in the u'v' chromaticity diagram.

FIG. 27 is an example showing the condition in which these types of main hatching and auxiliary hatching have been used together, and it can be seen that bottom right is horizontal/vertical indicating the case of gray.

[D] Other Preferred Embodiments, Modified Examples:

In the case of (D1) in which thin lines or text characters are present in the original document, since the hatching has poor visual recognizable condition, it is good to make it possible to recognize by carrying out hatching as described above for a few pixels of the background including the thin lines. Because of this, for thin lines (for example, text characters in red color), it is possible to make them recognizable by displaying that information by thin hatching in their surroundings.

In the case of (D2), in which the document has been generated electronically, the judgment for a uniform area, instead of judging by image processing for predetermined segmented areas, it is also good to use the object information of the document. In this case, wrong judgment will not be caused because information such as shading or hatching will be included.

(D3) The technology in each of the above preferred embodiments can be used not only in documents or images but also in screens for operation, etc., such as touch panels. In this case, it is also good to have a structure by which the user is made to select the method, etc. of adding hatching (contrast, or direction).

(D4) When carrying out half-toning in a printer (for example, dither processing or error dispersion processing, etc.), before half-toning, it is desirable to insert the above described hatching processing, or it is also good to set directly the angle in half-toning itself.

What is claimed is:

1. An information conversion method for adding textures to areas of an image where the areas have colors lying on a color confusion line, the method comprising:

deciding a first auxiliary line passing through a first position on the color confusion line and intersecting perpendicularly with the color confusion line and a second auxiliary line passing through a second position which is different from the first position on the color confusion line and intersecting perpendicularly with the color confusion line, with respect to the areas of the image having the colors lying on the color confusion line, wherein one of the first auxiliary line and the second auxiliary line is decided into a maximum and the other of the first auxiliary line and the second auxiliary line is decided into a minimum;

generating textures with different conditions according to a relative position on the color confusion line between the first auxiliary line and the second auxiliary line;

approximating an average color in each of the areas in which the textures are added to corresponding original colors; and adding the textures such that the average colors are approximated to the corresponding original colors of the image.

2. The information conversion method of claim 1, wherein the textures are added by changing an angle of a pattern of a texture.

3. The information conversion method of claim 1, wherein the textures are added by changing a contrast of a texture.

4. The information conversion method of claim 1, wherein the textures are added by changing a different cycle or speed of a texture.

5. The information conversion method of claim 1, wherein the textures are added by moving a texture in a different direction.

6. The information conversion method of claim 1, wherein the relative position is a position which is expressed with a ratio obtained by the following formula (1) as opposed to a distance between the first position and the second position on the color confusion line:

$$P\_b = BD/CD \tag{1}$$

where, $P\_b$ stands for the relative position;

BD stands for a distance between a predetermined position corresponding to which a texture is added and one of the first position and the second position on the color confusion line; and CD stands for the distance between the first position and the second position on the color confusion line.

7. The information conversion method of claim 1, wherein the added textures include textures in a state of continuous change.

8. The information conversion method of claim 1, wherein the textures are respectively added for the areas each of which comprises a plurality of pixels set previously.

9. The information conversion method of claim 1, wherein the areas are generated by segmenting the image in the form of a grid.

10. The information conversion method of claim 9, further comprising dividing each area into a plurality of segments according to a difference in color,
wherein the textures are added with angles that are different for every segment.

11. The information conversion method of claim 10, further comprising judging a presence or absence of noise or dither inside each area,
wherein the area is not divided into the plurality of segments when the presence of noise or dither is judged.

12. The information conversion method of claim 11, wherein the area is not divided into the plurality of segments when a color difference between neighboring pixels within the same area is judged to be less than a prescribed value.

13. The information conversion method of claim 1, further comprising printing out an inputted color image data by monochrome printing.

14. An information conversion apparatus for adding textures to areas of an image where the areas have colors lying on a color confusion line, the apparatus comprising:
a texture generating section which: (i) decides a first auxiliary line passing through a first position on the color confusion line and intersecting perpendicularly with the color confusion line and a second auxiliary line passing through a second position which is different from the first position on the color confusion line and intersecting perpendicularly with the color confusion line, with respect to the areas of the image having the colors lying on the color confusion line, wherein one of the first auxiliary line and the second auxiliary line is decided into a maximum and the other of the first auxiliary line and the second auxiliary line is decided into a minimum, and (ii) generates textures with different conditions according to a relative position on the color confusion line between the first auxiliary line and the second auxiliary line; and
an image processing section which approximates an average color in each of the areas in which the textures are added to corresponding original colors, and which adds the textures such that the average colors are approximated to the corresponding original colors of the image.

15. The information conversion apparatus of claim 14, wherein the texture generating section generates a texture by changing an angle of a pattern of the texture.

16. The information conversion apparatus of claim 14, wherein the texture generating section generates a texture by changing a contrast of the texture.

17. The information conversion apparatus of claim 14, wherein the textures are added by changing by a different cycle or speed of a texture.

18. The information conversion apparatus of claim 14, wherein the textures are added by moving a texture in a different direction.

19. The information conversion apparatus of claim 14, wherein the relative position is a position which is expressed with a ratio obtained by the following formula (1) as opposed to a distance between the first position and the second position on the color confusion line:

$$P\_b = BD/CD \tag{1}$$

where,
P_b stands for the relative position;
BD stands for a distance between a predetermined position corresponding to which a texture is added and one of the first position and the second position on the color confusion line; and
CD stands for the distance between the first position and the second position on the color confusion line.

20. The information conversion apparatus of claim 14, wherein the added textures include textures in a state of continuous change.

21. The information conversion apparatus of claim 14, wherein the textures are respectively added for the areas each of which comprises a plurality of pixels set previously.

22. The information conversion apparatus of claim 14, wherein the texture generating section generates the areas by segmenting the image in the form of a grid.

23. The information conversion apparatus of claim 22, wherein the texture generating section divides each area into a plurality of segments according to a difference in color, and wherein textures whose angles are different are added for every segment.

24. The information conversion apparatus of claim 23, wherein the texture generating section judges presence or absence of noise or dither inside each area, and does not divide the area into segments when presence of noise or dither is judged.

25. The information conversion apparatus of claim 24, wherein the texture generating section does not divide the area into segments when a color difference between neighboring pixels within the same area is judged to be less than a prescribed value.

26. The information conversion apparatus of claim 14, wherein the information conversion apparatus prints out an inputted color image data by monochrome printing.

27. A non-transitory computer readable recording medium having stored thereon an information conversion program which is executable by a computer for adding textures to areas of an image where the areas have colors lying on a color confusion line, the program being executed by the computer to perform functions comprising:
deciding a first auxiliary line passing through a first position on the color confusion line and intersecting perpendicularly with the color confusion line and a second auxiliary line passing through a second position which is different from the first position on the color confusion line and intersecting perpendicularly with the color confusion line, with respect to the areas of the image having the colors lying on the color confusion line, wherein one of the first auxiliary line and the second auxiliary line is decided into a maximum and the other of the first auxiliary line and the second auxiliary line is decided into a minimum;
generating textures with different conditions according to a relative position on the color confusion line between the first auxiliary line and the second auxiliary line;
approximating an average color in each of the areas in which the textures are added to corresponding original colors; and
adding the textures such that the average colors are approximated to the corresponding original colors of the image.

28. The non-transitory computer readable recording medium of claim 27, wherein the textures are added by changing an angle of a pattern of a texture.

29. The non-transitory computer readable recording medium of claim 27, wherein the textures are added by changing a contrast of a texture.

30. The non-transitory computer readable recording medium of claim 27, wherein the textures are respectively added for the areas each of which comprises a plurality of pixels set previously.

31. The non-transitory computer readable recording medium of claim 27, wherein the program is executed by the computer to print out an inputted color image data by monochrome printing.

* * * * *